US006991788B1

(12) United States Patent
Durden

(10) Patent No.: US 6,991,788 B1
(45) Date of Patent: Jan. 31, 2006

(54) **UTILIZATION OF *WOLINELLA SUCCINOGENES* ASPARAGINASE TO TREAT DISEASES ASSOCIATED WITH ASPARAGINE DEPENDENCE**

(75) Inventor: Donald L. Durden, Glendale, CA (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 105 days.

(21) Appl. No.: 10/349,374

(22) Filed: Jan. 21, 2003

Related U.S. Application Data

(63) Continuation of application No. 09/773,260, filed on Jan. 31, 2001, now abandoned, which is a continuation of application No. 09/094,435, filed on Jun. 9, 1998, now Pat. No. 6,251,388.
(60) Provisional application No. 60/049,085, filed on Jun. 9, 1997.

(51) Int. Cl.
| | | |
|---|---|---|
| *A61K 38/46* | (2006.01) | |
| *C12N 9/82* | (2006.01) | |
| *C12N 1/20* | (2006.01) | |
| *C12N 15/00* | (2006.01) | |
| *C07H 21/04* | (2006.01) | |

(52) U.S. Cl. .................. 424/94.6; 435/229; 435/252.3; 435/320.1; 536/23.2
(58) Field of Classification Search ................ 424/94.6; 435/229, 252.3, 320.1; 536/23.2
See application file for complete search history.

(56) References Cited

U.S. PATENT DOCUMENTS

| 5,322,678 A | 6/1994 | Morgan, Jr. et al. ....... 424/1.53 |
| 6,251,388 B1 | 6/2001 | Durden |

FOREIGN PATENT DOCUMENTS

| DE | 2039061 A | 2/1972 |
| EP | 0 211 639 A | 2/1987 |
| GB | 1264896 | 11/1968 |
| LU | 59710 A | 1/1970 |
| WO | WO 97/20041 | 11/1996 |

OTHER PUBLICATIONS

Martins et al. [Biochimie (1990): 72, 671–675].*
Ashworth et al., "Comparison of L–asparaginases from *Escherichia coli* and Erwinia carotovora as immunosuppressant," *Cancer Res.* 34:1353–1359 (1974).
Baechtel, F.S., et al., "The influence of glutamine, its decomposition products, and glutaminase on the transformation of human lymphocytes," *Biochem. Biophys. Acta* 421:33–43 (1976).
Broome, J.D., "Evidence that the asparaginase activity of guinea pig serum is responsible for its anti–lymphoma effects," *Nature* 191:1114–1115 (1961).
Broome, J.D., "Factors which may influence the effectiveness of L–asparaginase as tumor inhibitors," *Br. J. Cancer* 22:595–602 (1969).
Campbell, H.A., et al., "Two asparaginases from *Escherichia coli* B: their separation, purification, and anti–tumor activity," Biochemistry 6:721–730 (1967).
Cao, S. & Zhao, G., "Chemical modification of enzyme molecules to improve their characteristics," *Annals of the New York Academy of Sciences: Enzyme Engineering* $10^a$ 613:460–467 (1990).
Cheung, N. & Chau, K., "Antibody response to *Escherichia coli* L–asparaginase: Prognostic significance and clinical utility of antibody measurement," *Am. J. Pediatric Hematol. Oncol.* 8:99–104 (1986).
Clementi, A., "La desamidation enzmatique de l'asparagine chez les differentes especes–animals et la signification physiologique de sa presence dass l'organisme," *Arch. Intern. Physiol.* 19:369–398 (1922).
Cooney, D.A., et al., "L–asparaginase and L–asparagine metabolism," *Ann. Rev. Pharmacol.* 10:421–440 (1970).
Crowther, "L–Asparaginase and human malignant disease," Nature 229:168–171 (1971).
Distasio et al., "Glutaminase–free asparaginase from vibrio succinogenes: an antilymphoma enzyme lacking hepatotoxicity," *Int. J. Cancer* 30:343–347 (1982).
Distasio, J. & Niedennan, A., "Purification and characterization of L–asparaginase with anti–lymphoma activity from Vibrio succinogenes," *J. Biol. Chem.* 251:6929–6933 (1976).
Distasio, J.A., et al., "Alteration in spleen lymphoid populations associated with specific amino acid depletion during L–asparaginase treatment," *Cancer Res.* 42:252–258 (1982).
Durden, D.L. & Distasio, J.A., "Characterization of the effects of asparaginases from *Escherichia coli* and a asparaginase from Vibrio succinogenes on specific cell–mediated cytotoxicity," *Int. J. Cancer* 27:59–65 (1981).

(Continued)

*Primary Examiner*—Tekchand Saidha
(74) *Attorney, Agent, or Firm*—Perkins Coie LLP

(57) ABSTRACT

Described herein are methods for producing recombinant forms of asparaginase derived from *Wolinella succinogenes*. In addition, methods for covalent modification of proteins, including asparaginases, by acylation are also provided. Certain embodiments provide for epitopic-labeling of the amino terminus of *W. succinogenes* asparaginase. Additional embodiments concern methods for the therapeutic utilization of the native, homotetrameric form of *W. succinogenes* asparaginase, as well as the use of epitopically-labeled or non-epitopically-labeled recombinant *W. succinogenes* asparaginase (or a covalently modified analog thereof) in the therapeutic treatment of malignant and non-malignant hematological disease and other diseases where asparagine depletion or deprivation would be efficacious or which respond to asparagine depletion or deprivation, as well as their potential utilization in the therapeutic treatment of autoimmune diseases such as rheumatoid arthritis, AIDS, and SLE.

10 Claims, 7 Drawing Sheets

OTHER PUBLICATIONS

Durden, D.L., "A glutaminase–free asparaginase from Vibrio succinogenes lacking immunosuppression and toxicity," *Ph.D. Dissertation, University of Miami Medical School* (1983).

Durden, D.L., "Kinetic analysis of hepatotoxicity associted with anti–neoplastic asparaginases," *Cancer Res.* 43:1602–1605 (1983).

El–Asmar, F.A. & Greenberg, D.H., "Studies on the mechanism of inhibition of tumor growth by glutaminase," *Cancer Res.* 26:116–122 (1966).

Gardner et al., "Lymphoid tumors in mice receiving steroid hormones," *Cancer Research* 4:73–87 (1944).

Habeeb, A.F.S.A., "Determination of free amino groups in proteins by trinitrobenzenesulfonic acid," Analytical Biochemistry 14:328–336 (1966).

Harlow and Lane in *Antibodies, a Laboratory Manual*, Cold Spring Harbor Laboratory, 1988.

Hersh, E.M. & Brown, B.W., "Inhibition of immune response by glutamine antagonism: effect of azotomycin on lymphocyle blastogenesis," *Cancer Res.* 31:834–840 (1980).

Hersh, "L–Glutaminase: Suppression of lymphocyte blastogenic responses in vitro," *Science* 172:736–738 (1971).

Hochuli et al., "New metal chelate absorbents selective for protein and peptide containing neighboring histidine residues," J. Chromatography 411:177–184 (1987).

Howard, J. B & Carpenter, F.H., "L–asparaginase from Erwinia carotovora: substrate specificity and enzymatic properties," *J. Biol. Chem.* 247:1020–1030 (1972).

Jack et al., "The effect of histidine ammonia–lyase on some murine tumors," *Leukemia Res.* 7:421 (1983).

Lubkowski et al., "Crystal structure and amino acid sequence of Wolinella succinogenes L–asparaginase," *Eur. J. Biochem.* 241:201–207 (1996).

*Molecular Cloning, A Laboratory Manual*, 2d ed., ed. Sambrook, et al., Cold Spring Harbor Laboratory Press (1989) (Table of contents only).

Ohno, R. & Hersh, E. M., "Immunosuppressive effects of L–asparaginase," *Cancer Res.* 30:1605–1611 (1970).

Ortega, J.A., et al., "L–asparaginase, vincristine, and prednisone for the induction of first remission in acute lymphocytic leukemia," Cancer Res. 37:535–540 (1977).

Park, R & Liu, K., "A role for Shc, grb2 and raf–1 in FcR1 signal relay," J. Biol. Chem. 271:13342–13348 (1996).

Schein et al., "The toxicity of *E. coli* asparaginase," *Cancer Res.* 29:426–434 (1969).

Schrek, R., et al., "Effect of L–glutaminase on transformation and DNA synthesis of normal lymphocytes," *Acta Haematol.* 48:12–15 (1972).

Schwartz, R.S., "Immunosuppression by L–asparaginase," *Nature* 224:275–276 (1969).

Simberkoff, M.S. & Thomas, L., "Reversal by L–glutamine of the inhibition of lymphocyte mitosis caused by *E. coli* asparaginase," *Proc. Soc. Exp. Biol.* 133 642–644 (1970).

Spiers, A.D.S., et al., "L–glutaminase/L–asparaginase: human pharmacology, toxicology, and activity in acute leukemia," *Cancer Treat. Rep.* 63:1019–1024 (1979).

Pastor et al., "Treatment of systemic lupus erythematosus with L–asparaginase: considerations on a case," Revista do Hospital das Clinicas; Faculdade de Medicina da Universidade Sao Paulo, vol. 27, No. 3, pp. 129–133, May–Jun. 1972.

Rudinger, In Peptide Hormones, Parsons, Ed., pp. 2, 4 and 5, Jun. 1976.

Guan et al., "Primary cloining and expression fo the Vibrio succinogenes L–asparaginase gene," Shengwu Gongcheng Xuebao, vol. 4, No. 1, pp. 11–19, 1988.

Guan et al., "Primary cloning and expression of a gene encoding the antileukemia agent (asparaginase)," Chin. Sci. Bull., vol. 34, No. 5, pp. 436–437, 1989.

Guan et al., "Primary cloning and expression of the Vibrio succinogenes L–asparaginase gene," Shengwu Gongcheng Xuebao, vol. 4, No. 1, pp. 11–19, 1988.

Wada et al., Antitumor Enzyme: Polyethylene glycol—Modified Asparaginase, Ann. NY Acad. Sco., vol. 613, pp. 96–108, 1990.

Ngo et al., "Computational Complexity, Protein Structure Prediction, and the Levinthal Paradox," In The Protein folding Provblem and Terriary Structure Prediction, Merz, Jr. et al., Eds., Birkhauser Boston, pp. 492–494, 1994.

Thornton et al., "Protein Engineering", Curr. Opinion in Biotech, vol. 6, No. 4, pp. 367–369, Aug. 1995.

Eur. J. Biochem. (Oct. 1, 1996) 241 (1) : 201–207.

Journal of Biological Chemistry, (1976) 251/22 (6929–6933).

Abuchowski, A., et al., "Cancer Therapy with Chemically Modified Enzymes. I. Antitumor Properties of Polyethylene Glycol–Asparaginase Conjugates," *Cancer Biochem Biophys* 1984; 7:175–186.

Durden, D.L., Distasio, J.A., "Comparison of the Immunosuppressive Effects of Asparaginases from *Escherichia coli* and Vibrio succinogenes," *Cancer Res* 1980; 40:1125–1129.

Veronese, F.M., et al., "Improvement of Pharmacokinetic, Immunological, and Stability Properties of Asparaginase by Conjugation to Linear and Branched Monomethoxy Poly–(Ethylene Glycol)," *J Controlled Release* 1996; 40:199–209.

* cited by examiner

[SEQ ID NO. 1] - FORWARD PCR PRIMER (BamHI SITE UNDERLINED)

5'-TCC<u>GGATCC</u>AGCGCCTCTGTTTTGATGGCT-3'

[SEQ ID NO. 2] - REVERSE PCR PRIMER (EcoRI SITE UNDERLINED)

5'-TGG<u>GAATTC</u>GGTGGAGAAGATCTTTTGGAT-3'

```
ATG GGC AGC AGC CAT CAT CAT CAT CAT CAT AGC AGC GGC CTG GTG CCG
CGC GGC AGC CAT ATG GCT AGC ATG ACT GGT GGA CAG CAA ATG GGT CGC
GGA TCC AGC GCC TCT GTT TTG ATG GCT AAA CCC CAA GTG ACT ATC CTA
GCC ACA GGA GGC ACC ATC GCT GGT TCG GGG GAA TCT AGC GTC AAG AGT
AGC TAC TCT GCT GGA GCA GTC ACC GTT GAT AAG CTT CTT GCA GCC GTC
CCT GCC ATC AAC GAC CTA GCC ACC ATC AAG GGT GAA CAG ATC TCA AGC
ATT GGC TCC CAA GAG ATG ACG GGT AAG GTG TGG CTT AAA CTA GCC AAG
CGT GTC AAT GAG CTC CTC GCC CAA AAA GAG ACC GAA GCC GTG ATC ATC
ACC CAT GGA ACT GAC ACC ATG GAA GAG ACC GCT TTC TTC CTC AAC CTC
ACG GTG AAA AGC CAA AAA CCT GTC GTC CTT GTA GGC GCC ATG CGT CCA
GGC TCT TCC ATG AGT GCT GAT GGC CCC ATG AAT CTC TAT AAC GCC GTG
AAT GTA GCG ATC AAC AAA GCC TCT ACT AAC AAA GGA GTG GTG ATT GTG
ATG AAC GAT GAG ATT CAC GCC GCC AGA GAA GCG ACC AAG CTC AAC ACC
ACC GCA GTC AAT GCA TTT GCT TCG CCC AAC ACA GGT AAA ATC GGC ACA
GTC TAT TAT GGC AAA GTC GAG TAT TTC ACT CAA TCC GTT CGA CCT CAC
ACC CTT GCA AGT GAG TTT GAT ATT AGC AAA ATC GAA GAA CTC CCC AGA
GTC GAT ATT CTT TAC GCT CAC CCC GAT GAT ACT GAT GTT TTA GTC AAT
GCA GCC CTT CAG GCA GGA GCC AAA GGA ATC ATC CAT GCA GGC ATG GGC
AAT GGG AAC CCT TTC CCT TTG ACT CAA AAT GCT CTT GAA AAA GCA GCC
AAA TCA GGC GTA GTC GTC GCT CGA AGC TCT AGA GTG GGC AGT GGT TCC
ACC ACC CAA GAG GCT GAA GTG GAT GAT AAG AAA CTT GGT TTT GTG GCT
ACA GAG AGT CTC AAC CCT CAA AAA GCC AGA GTG CTT CTT ATG TTA GCC
CTC ACC AAA ACT AGT GAT AGA GAG GCG ATC CAA AAG ATC TTC TCC ACC
TAT TAA TCCAAGAAAGGGAATCTCTTCAC
```

THE POLYCAT SEQUENCE WHICH ENCODES THE POLYHISTIDINE RESIDUES, THE ATG START SITE, AND THE TAA STOP CODON ARE SHOWN IN BOLD LETTERS.

FIG. 7.

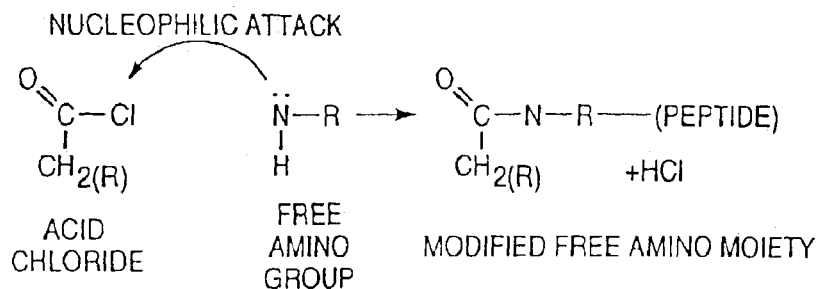

pH 8.5 TO MAINTAIN PORTONATED STATE OF NITROGEN ATOM

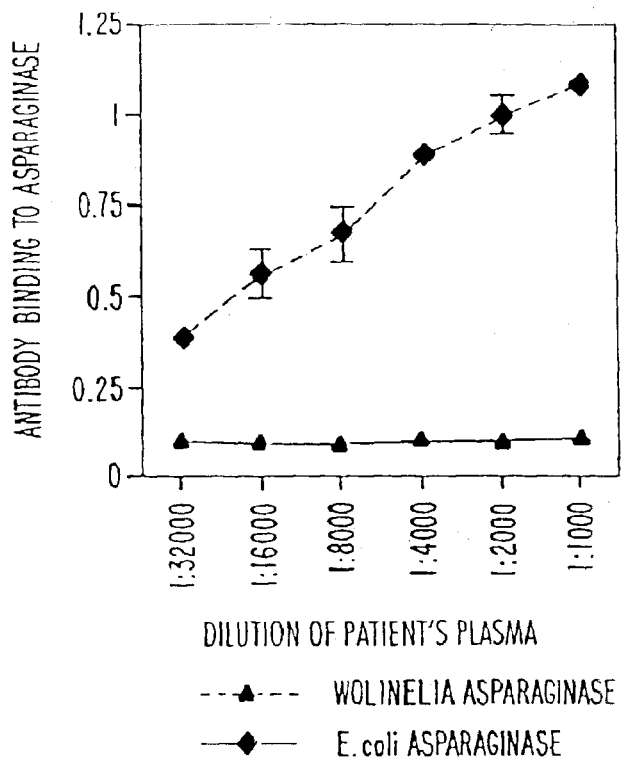
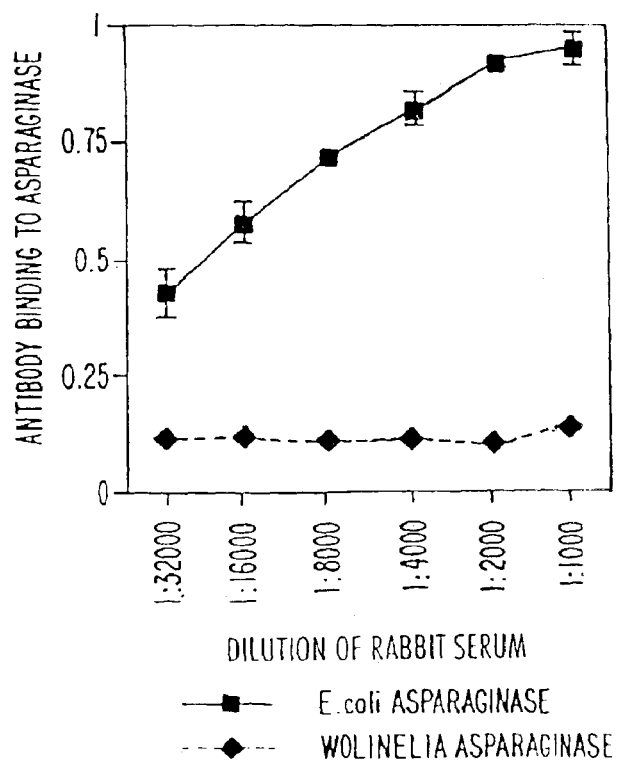

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 30 base pairs
      (B) TYPE: nucleic acid

```
        (C) STRANDEDNESS: single
        (D) TOPOLOGY: linear (xi) SEQUENCE DESCRIPTION: SEQ ID NO: 1:

TCCGGATCCA GCGCCTCTGT TTTGATGGCT                                  30

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 2:

TGGGAATTCG GTGGAGAAGA TCTTTTGGAT                                  30

(2) INFORMATION FOR SEQ ID NO: 3:

(i) SEQUENCE CHARACTERISTICS:
        (A) LENGTH: 1133 base pairs
        (B) TYPE: nucleic acid
        (C) STRANDEDNESS: single
        (D) TOPOLOGY: linear (xi) SEQUENCE DESCRIPTION: SEQ ID NO: 3:

ATGGGCAGCA GCCATCATCA TCATCATCAT AGCAGCGGCC TGGTGCCGCG CGGCAGCCAT    60

ATGGCTAGCA TGACTGGTGG ACAGCAAATG GGTCGCGGAT CCAGCGCCTC TGTTTTGATG   120

GCTAAACCCC AAGTGACTAT CCTAGCCACA GGAGGCACCA TCGCTGGTTC GGGGGAATCT   180

AGCGTCAAGA GTAGCTACTC TGCTGGAGCA GTCACCGTTG ATAAGCTTCT TGCAGCCGTC   240

CCTGCCATCA ACGACCTAGC CACCATCAAG GGTGAACAGA TCTCAAGCAT TGGCTCCCAA   300

GAGATGACGG GTAAGGTGTG GCTTAAACTA GCCAAGCGTG TCAATGAGCT CCTCGCCCAA   360

AAAGAGACCG AAGCCGTGAT CATCACCCAT GGAACTGACA CCATGGAAGA GACCGCTTTC   420

TTCCTCAACC TCACGGTGAA AAGCCAAAAA CCTGTCGTCC TTGTAGGCGC CATGCGTCCA   480

GGCTCTTCCA TGAGTGCTGA TGGCCCCATG AATCTCTATA ACGCCGTGAA TGTAGCGATC   540

AACAAAGCCT CTACTAACAA AGGAGTGGTG ATTGTGATGA ACGATGAGAT TCACGCCGCC   600

AGAGAAGCGA CCAAGCTCAA CACCACCGCA GTCAATGCAT TTGCTTCGCC CAACACAGGT   660

AAAATCGGCA CAGTCTATTA TGGCAAAGTC GAGTATTTCA CTCAATCCGT TCGACCTCAC   720

ACCCTTGCAA GTGAGTTTGA TATTAGCAAA ATCGAAGAAC TCCCCAGAGT CGATATTCTT   780

TACGCTCACC CCGATGATAC TGATGTTTTA GTCAATGCAG CCCTTCAGGC AGGAGCCAAA   840

GGAATCATCC ATGCAGGCAT GGGCAATGGG AACCCTTTCC CTTTGACTCA AAATGCTCTT   900

GAAAAAGCAG CCAAATCAGG CGTAGTCGTC GCTCGAAGCT CTAGAGTGGG CAGTGGTTCC   960

ACCACCCAAG AGGCTGAAGT GGATGATAAG AAACTTGGTT TTGTGGCTAC AGAGAGTCTC  1020

AACCCTCAAA AAGCCAGAGT GCTTCTTATG TTAGCCCTCA CCAAAACTAG TGATAGAGAG  1080

GCGATCCAAA AGATCTTCTC CACCTATTAA TCCAAGAAAG GGAATCTCTT CAC         1133
```

UTILIZATION OF *WOLINELLA SUCCINOGENES* ASPARAGINASE TO TREAT DISEASES ASSOCIATED WITH ASPARAGINE DEPENDENCE

This application is a continuation of U.S. patent application Ser. No. 09/773,260, filed Jan. 31, 2001, and now abandoned; which is a continuation of U.S. patent application Ser. No. 09/094,435, filed Jun. 9, 1998, now U.S. Pat. No. 6,251,388 B1; which claims benefit of U.S. Provisional Application Ser. No. 60/049,085, filed Jun. 9, 1997, all of which are incorporated herein by reference.

FIELD OF INVENTION

The present invention relates to methodologies for the production of microbial enzymes, particularly native and recombinant *Wolinella succinogenes* asparaginase and its analogs, which possesses potent in vitro and in vivo activity against diseases correlated with asparagine dependence. In addition, the present invention also relates to methods for the utilization of recombinant microbial enzymes in the treatment of diseases which respond to asparagine depletion, including various hematologic, autoimmune, and infectious diseases.

BACKGROUND OF INVENTION

The references cited below are not admitted to be prior art to the inventions described herein.

Asparaginases are enzymes which catalyze the deamidation of L-asparagine (asparaginase activity) and L-glutamine (glutaminase activity). See Cantor, P. S. & Schimmell, M. R., *Enzyme Catalysis, 2nd ed.,* (T. Pettersonn & Y. Tacashi, eds.) Sanders Scientific Press, New York pp. 219–23. (1990). L-glutamine serves as the amide donor in purine biosynthesis, as well as other transamination reactions, and hence plays a role in DNA and cyclic nucleotide metabolism.

In vivo biochemical activity of asparaginase was first documented to be present in guinea pig serum in 1922 (see Clementi, A., La desamidation enzmatique de l'asparagine chez les differentes especes-animals et la signification physiologique de sa presence dass l'organisme, 19 *Arch. Intern. Physiol.* 369 (1922)). The subsequent discovery that asparaginase isolated from guinea pig serum was the active agent which inhibited the in vivo growth of certain asparagine-dependent mammalian tumors without concomitant deleterious effects on normal tissue (see Broome, J. D., Evidence that the asparaginase activity of guinea pig serum is responsible for its anti-lymphoma effects, 191 *Nature* 1114 (1961)) suggested that this enzyme could be utilized as an anti-neoplastic agent. Because L-asparagine is a non-essential amino acid, asparaginase was initially thought to represent a unique prototype of selective chemotherapy in which treatment could be directed specifically and selectively against asparagine-dependent cells. However, the low levels of asparaginase in guinea pig serum necessitated the development of a more practical source of this anti-neoplastic enzyme.

Subsequently, microbial asparaginase isolated from *Escherichia coli* and *Erwinia carotovora* were shown to act as potent anti-leukemic agents (see Howard, J. B. & Carpenter, F. H., L-asparaginase from *Erwinia carotovora;* substrate specificity and enzymatic properties, 247 *J. Biol. Chem.* 1020 (1972); Campbell, H. A., et al., Two asparaginases from *Escherichia coli* B: their separation, purification, and anti-tumor activity, 6 *Biochemistry* 721 (1967)), and when one of these enzymes was utilized in combination with the chemotherapeutic agent vincristine and the corticosteroid prednisone for the treatment of acute lymphoblastic or acute undifferentiated human leukemia, an overall remission rate of 93% was reported (see Ortega, J. A., et al., L-asparaginase, vincristine, and prednisone for the induction of first remission in acute lymphocytic leukemia, 37 *Cancer Res.* 535 (1977)).

While these asparaginases possess potent anti-leukemic activity, clinical utilization of the aforementioned microbial asparaginases resulted in a wide range of host toxicity (e.g., hepatic, renal, splenic, pancreatic dysfunction and blood coagulation) and pronounced immunosuppression (see Ohno, R. & Hersh, E. M., Immunosuppressive effects of L-asparaginase, 30 *Cancer Res.* 1605 (1970)), unlike asparaginase isolated from guinea pig serum (see Cooney, D. A., et al., L-asparaginase and L-asparagine metabolism, 10 *Ann. Rev. Pharmacol.* 421 (1970)).

Examination of the effects of *E. coli* asparaginase treatment on spleen histology and lymphocyte populations revealed a marked reduction in both the size and reactivity of the splenic germinal centers which was concomitantly associated with a marked reduction in the cytoplasmic immunoglobulin-containing cells (B-cell immunoblasts; see Distasio, J. A., et al., Alteration in spleen lymphoid populations associated with specific amino acid depletion during L-asparaginase treatment, 42 *Cancer Res.* 252 (1982)). Additionally, examination of the lymphocyte sub-population within the spleen revealed that there was a 40% reduction in the percentage of surface immunoglobulin-expressing cells (B-cells) accompanied by an increase in the ratio of Thy-1.2-expressing cells (T-cells), whereas the ratio of Lyt-2 to Lyt-1 cells remained unchanged in comparison to the control animal group. These results supported the hypothesis that glutamine, or glutamine combined with asparagine depletion initially resulting from administration of *E. coli* asparaginase, caused a marked decrease in spleen lymphocytic cells of the B-cell lineage.

Another important adverse clinical effect associated with traditional microbial asparaginase treatment is hepatic dysfunction (see Schein, P. S., et al., The toxicity of *E. coli* asparaginase, 29 *Cancer Res.* 426 (1969)). Patients treated with *E. coli* asparaginase generally exhibit decreased plasma levels of albumin, antithrombin III, cholesterol, phospholipids, and triglycerides. Other indications of asparaginase-induced hepatic dysfunction and pathology include fatty degenerative changes, delayed bromosulfophthalein clearance, and increased levels of serum glutamic-oxaloacetic transaminase and alkaline phosphatase. Although some investigators have reported that low dosages of *E. coli* asparaginase result in limited hepatotoxic complications, sensitive indicators of hepatic function in some patients receiving low dosages, however, still reveals significant hepatic disease which may result in life-threatening coagulopathy (see Crowther, D., Asparaginase and human malignant disease, 229 *Nature* 168 (1971)).

The hepatotoxic effects of microbial asparaginases may be a result of their capability to hydrolyze both asparagine and glutamine. One biochemical difference between *E. coli* and *E. carotovora* asparaginases and the enzyme derived from guinea pig is the non-specific amidohydrolase activity associated with the microbial enzymes (see Howard, J. B. & Carpenter, F. H., (1972) supra; Campbell, H. A., et al., (1967) supra). For example, *E. coli asparaginase has been shown to possess a* 130-fold greater level of glutaminase activity as compared to the activity of *Wolinella succinogenes* (previously classified as *Vibrio succinogenes*) asparaginase. As a result, patients treated with the conventional microbial asparaginases show a marked reduction in serum levels of both glutamine and asparagine (see Schrek, R., et al., Effect of L-glutaminase on transformation and DNA synthesis of normal lymphocytes, 48 *Acta Haematol.* 12 (1972)), which may demonstrate a possible correlation between glutamine deprivation and asparaginase-induced clinical toxicity (see Spiers, A. D. S., et al., L-glutaminase/L-asparaginase: human pharmacology, toxicology, and activity in acute leukemia, 63 *Cancer Treat. Rep.* 1019 (1979)).

The relative importance of L-glutamine in mammalian intermediary metabolism served to stimulate further research into the possible role of glutamine deprivation in asparaginase-induced immunosuppression. Lymphoid tissue has been shown to have relatively low levels of glutamine synthetase activity (see El-Asmar, F. A. & Greenberg, D. H., Studies on the mechanism of inhibition of tumor growth by glutaminase, 26 *Cancer Res.* 116 (1966); Hersh, E. M., L-glutaminase: suppression of lymphocyte blastogenic responses in vitro. 172 *Science* 139 (1971)), suggesting that these tissues may be particularly sensitive to the depletion of exogenous glutamine. In contrast, some investigators have proposed that asparagine depletion alone may be responsible for asparagine-induced immunosuppression (see Baechtel, F. S., et al., The influence of glutamine, its decomposition products, and glutaminase on the transformation of human lymphocytes, 421 *Biochem. Biophys. Acta* 33 (1976)).

While the immunosuppressive effect of *E. coli* and *E. carotovora* asparaginases are well-documented (see Crowther, D., (1971) supra; Schwartz, R. S., Immunosuppression by L-asparaginase, 224 *Nature* 276 (1969)), the molecular biological basis of these functions have not yet been fully elucidated. The inhibition of lymphocyte blastogenesis by various L-glutamine antagonists (see Hersh, E. M. & Brown, B. W., Inhibition of immune response by glutamine antagonism: effect of azotomycin on lymphocyte blastogenesis, 31 *Cancer Res.* 834 (1980)) and glutaminase from *Escherichia coli* (see Hersh, E. M., (1971) supra) tends to be illustrative of a possible role for glutamine depletion in immunosuppression. It has been also demonstrated that inhibition of the lymphoid blastogenic response to phytohemagglutinin (PHA) by *E. coli* asparaginase can be reversed by the addition of L-glutamine but not by the addition of L-asparagine. See Simberkoff, M. S. & Thomas, L., Reversal by L-glutamine of the inhibition of lymphocyte mitosis caused by *E. coli* asparaginase, 133 *Proc. Soc. Exp. Biol.* (*N. Y.*) 642 (1970). Additionally, a correlation between immunosuppression and the relative amount of glutaminase activity has been suggested by the observation that E. asparaginase is more effective than *E. coli* asparaginase in suppressing the response of rabbit leukocytes to PHA (see Ashworth, L. A. E. & MacLennan, A. P., Comparison of L-asparaginases from *Escherichia coli* and *Erwinia carotovora as immunosuppressant,* 34 *Cancer Res.* 1353 (1974)). However, the significance of these in vitro studies is somewhat limited because the in vivo fates of asparaginases and the homeostatic control of asparagine and glutamine may result in a modification of the immunosuppressive effects of anti-neoplastic asparaginases.

Another significant problem associated with the use of microbial asparaginases is that patients treated with *E. coli* and *E. carotovora* asparaginases frequently develop neutralizing antibodies of the IgG and IgM immunoglobulin class (see, e.g., Cheung, N. & Chau, K., Antibody response to *Escherichia coli* L-asparaginase: Prognostic significance and clinical utility of antibody measurement, 8 *Am. J. Pediatric Hematol. Oncol.* 99 (1986); Howard, J. B. & Carpenter, F. H. (1972) supra), which allows an immediate rebound of serum levels of asparagine and glutamine. In an attempt to mitigate both the toxic effects and immunosensitivity associated with the therapeutic utilization of *E. coli* and *E. carotovora* asparaginase, a covalently-modified *E. coli* asparaginase (PEG-asparaginase) was initially developed for use in patients who have developed a delayed-type hypersensitivity to preparations "native" of *E. coli* asparaginase (see Gao, S. & Zhao, G., Chemical modification of enzyme molecules to improve their characteristics, 613 *Ann. NY Acad. Sci.* 460 (1990)). However, subsequent studies established that the initial development of an immune response against *E. coli* asparaginase resulted in an 80% cross-reactivity against the PEG-asparaginase with concomitant adverse pharmacokinetic effects—neutralization of PEG-asparaginase activity and normalization of the plasma levels of L-asparagine and L-glutamine (see Avramis, V. & Periclou, I., Pharmodynamic studies of PEG-asparaginase (PEG-ASNase) in pediatric ALL leukemia patients, *Seventh International Congress on Anti-Cancer Treatment,* Paris, France (1997)). The development of antibodies directed against *E. coli* (EC) asparaginase and the modified PEG-asparaginase in patients is associated with neutralization of the enzymatic activity of both the EC and PEG-asparaginases in vivo, thus potentially resulting in an adverse clinical prognosis.

It is the object of this invention to solve the foregoing problems through the provision of a therapeutically effective and immunologically-distinct, alternative form of asparaginase, i.e., *W. succinogenes* asparaginase or an analog thereof. Such asparaginases and their preparation are described in detail below, and they can be used to treat patients suffering from diseases responded to asparagine deprivation as first line therapy or, alternatively, to treat patients who had previously developed hypersensitization to other microbial asparaginases, e.g., that derived from *E. coli,* and/or modified forms of non-*W. succinogenes* asparaginases, e.g., *E. coli* or *E. carotovora* asparaginase that has been pegylated.

DEFINITION OF TERMS

Unless otherwise expressly defined, the terms used herein will be understood according to their ordinary meaning in the art, although the following terms will be understood to have the following meanings, unless otherwise indicated.

An "analog" of a protein, e.g., asparaginase, refers to a polypeptide which differs in some way from it form(s) found naturally. For example, in certain embodiments, an analog of asparaginase will refer to an enzyme wherein one or more amino acids has been deleted from the naturally occurring amino acid sequence. Alternatively, one or more amino acid residues may be substituted with a different amino acid. Other analogs include those wherein additional amino acids have been added to the native sequence. For example, one or more amino acids may be added to the amino terminus and/or carboxy-terminus of the enzyme, or be inserted between internal amino acid residues. Such analogs can be prepared by any suitable technique, although modifying a recombinant gene to encode the desired change(s) will typically be employed. Other analogs include those wherein one or more amino acid residues are derivatized, e.g., glycosylated, pegylated, acylated or otherwise bound covalently to a molecule not attached to native forms of the protein. Of course, analogs according to the invention include those wherein an amino acid residue is added to or substituted in the native amino acid sequence, and this new residue is itself later modified, for example, by a covalent modification performed after the enzyme has been at least partially purified or isolated. Moreover, as used herein, an asparaginase analog includes those that have been modified and exhibit altered biochemical or physiological properties, e.g., different substrate specificity and/or affinity, altered quarternary structure, etc. After generating analogs, e.g., by a rational design strategy, random mutagenesis, etc., the proteins can be screened for biological activity, as described elsewhere herein. When large numbers of analogs are generated, high throughput screen methods are preferred. Those proteins found to exhibit the desired activity in vitro may then be tested in vivo for activity and pharmacokinetic properties.

A "unique contiguous amino acid sequence" means an amino acid sequence not found in a naturally occurring protein or polypeptide. Thus, a "unique contiguous amino acid sequence of *Wolinella succinogenes*" refers to a sequence which contains one or more amino acid substitutions, insertions, or deletions, as compared to corresponding region of the native enzyme.

A "disease which responds to asparagine depletion" refers to a disorder wherein the cells responsible for the disease state either lack or have a reduced ability to synthesize asparagine. Depletion or deprivation of asparagine to such cells can be partial or substantially complete, so long as the desired therapeutic benefit is achieved. In certain embodiments, more than about 50% of asparagine in the serum is depleted, preferably greater than about 75%, with depletion of more than 95% being most preferably achieved. Representative examples of diseases which respond to asparagine depletion or deprivation include certain malignant diseases, particularly malignant hematologic diseases, including lymphomas, leukemias and myelomas. Particular examples of leukemias treatable according to the invention include acute lymphoblastic leukemia (ALL), acute non-lymphocytic leukemias, B-cell and T-cell leukemias, chronic leukemias, and acute undifferentiated leukemia. Representative non-malignant hematologic diseases which respond to asparagine depletion immune system-mediated blood diseases, e.g., infectious diseases such as those caused by HIV infection (i.e., AIDS). Non-hematologic diseases associated with asparagine dependence include autoimmune diseases, for example rheumatoid arthritis, SLE, autoimmune, collagen vascular diseases, AIDS, etc. Other autoimmune diseases include osteo-arthritis, Issac's syndrome, psoriasis, insulin dependent diabetes mellitus, multiple sclerosis, sclerosing panencephalitis, systemic lupus erythematosus, rheumatic fever, inflammatory bowel disease (e.g., ulcerative colitis and Crohn's disease), primary billiary cirrhosis, chronic active hepatitis, glomerulonephritis, myasthenia gravis, pemphigus vulgaris, and Graves' disease. Notwithstanding the foregoing, any disease the cells responsible for which respond, e.g., cease proliferating, become senescent, undergo apotosis die, etc., to asparagine depletion may be treated in accordance with the instant methods. As those in the art will appreciate, cells suspected of causing disease can be tested for asparagine dependence in any suitable in vitro or in vivo assay, e.g., an in vitro assay wherein the growth medium lacks asparagine.

A "patient" refers to an animal afflicted with a disease which responds to asparagine depletion. Typically, patients treated in accordance with the instant methods are mammals, e.g., bovine, canine, equine, feline, ovine, porcine, and primate animals, particularly humans.

An "expression vector" refers to a nucleic acid, typically a plasmid, into which heterologous genes of interest may be cloned and subsequently expressed. For expression, such vectors are generally introduced into a suitable host cell or population of host cells. The expression vector can be introduced by any appropriate technique. Preferred techniques include transformation, electroporation, transfection, and ballistic (e.g., "gene gun") introduction. Depending upon the vector employed, suitable host cells for expression of the desired heterologous gene(s) include prokaryotic and eukaryotic cells. Preferred prokaryotic cells are transformation-competent bacterial cells such as *E. coli* strain and DH5α and JM 109. Preferred eukaryotic host cells include yeast and mammalian cell lines. As those in the art will appreciate, the particular expression vector/host cell system selected for expression of the desired heterologous gene depends on many factors, and is left to the skilled artisan to determine in the particular circumstances. Similarly, the conditions required for expression of the desired gene from an expression vector carrying the same depends on many factors, including the host cell type, the promoter(s) and other transcription regulation elements employed, the media (or medium) used, etc., Again, the selection made in a given circumstance is at the discretion of the artisan involved, and the particular employed is readily within the skill of such a person given the disclosure herein.

A protein which is "biologically active" is one which has at least one of the biological activities of the corresponding native protein, although the activity exhibited may differ in degree from that of the native protein. For example, an analog of *W. succinogenes* according to the invention may have a greater specific activity, longer serum half-life, etc. than the native form of the protein.

A protein which comprises an "epitope-tag" refers to one having one or more, preferably two or more, additional amino acids covalently attached thereto, which tag has a distinct epitope which can be recognized by another protein, e.g., an antibody which binds that epitope, preferably with high affinity, a protease which cleaves in or around a specific amino acid sequence (e.g., DAPI, cathepsin-C), etc. For example, as used herein an "N-terminal epitope tag" can refer to a peptide attached to the N-terminus of a protein, wherein the peptide has a conformation recognized by a particular antibody. Such a peptide and its corresponding antibody(ies) can be used to rapidly purify the polypeptide to which the peptide is attached by standard affinity chromatography techniques. Such antibodies, and any others used in the practice of this invention (e.g., for targeting gene delivery vehicles), can be prepared used techniques widely known in the art. For example, see Harlow and Lane in *Antibodies, a Laboratory Manual,* Cold Spring Harbor Laboratory, 1988. Epitope tags may also be included at the C-terminus of the protein, and in internal regions where insertion of such a tag does not substantially and adversely affect the biological activity or pharmacokinetic properties of the enzyme.

A "therapeutically effective amount" of a protein (e.g., an asparaginase or analog thereof) means that amount required to produce the desired therapeutic effect. Of course, the actual amount required depends on many factors, such as the disease to be treated, the progression of the disease, the age, size, and physical condition of the patient, as discussed in more detail below.

By "altering a pharmacokinetic property of a protein" is meant that a property of a drug as it acts in the body over a period of time, e.g., serum half-life, clearance rate, biodistribution, immunogenecity, etc., is changed. Such alteration can be either an increase or decrease in the property being examined.

SUMMARY OF THE INVENTION

One aspect of the invention provides methods for isolating native, homotetrameric asparaginase (WS) derived from *Wolinella succinogenes* (previously classified as *Vibrio succinogenes*).

Another aspect of the invention concerns methods for producing recombinant asparaginase (rWS) derived from *W. succinogenes*, particularly analogs thereof. In certain embodiments, such methods involve obtaining nucleic acid coding for a polypeptide comprising unique contiguous amino acid sequence of *W. succinogenes* asparaginase, wherein such amino acid sequence comprises at least nine amino acids, cloning that nucleic acid into an expression vector, introducing the expression vector into an appropriate host cell or population of host cells, culturing the host cell(s) under conditions which allow expression of the polypeptide (here, a *W. succinogenes* analog) in a biologically active form, or a form from which biological activity can be reconstituted. In preferred embodiments, the nucleic acid molecule codes for a *W. succinogenes* asparaginase analog wherein at least one amino acid of the native protein has been substituted with another amino acid residue or deleted, and/or one or more additional amino acids have been inserted. Particularly preferred embodiments of this aspect concern methods for producing analogs which contain an epitope tag, preferably an N-terminal epitope tag. A representative nucleic acid useful in this context comprises the nucleotide sequence set forth in SEQ ID NO:3. As those in the art will appreciate, an epitope-tag, e.g., an N-terminal epitope-tag, can be especially useful during purification of the enzymes.

Proteins (including native and recombinant *W. succinogenes* asparaginase, analogs and derivatives thereof, and acylated asparaginases derived from other sources) produced in accordance with the foregoing methods can be purified and formulated into pharmaceutical compositions. Purification can be accomplished by any suitable process. Such processes typically involve affinity purification processes and/or size separation techniques. After purification, the polypeptide can be formulated into a pharmaceutical composition comprising the enzyme and a pharmaceutically acceptable carrier. Such compositions, and others according to the invention, are the administered to a patient so as to deliver a therapeutically effective amount of the enzyme. In certain embodiments, such compositions allow for oral delivery, while other embodiments allow for transdermal or transmucosal delivery. Preferred embodiments include those intended for parenteral injection, e.g., via an intramuscular, intravenous or subcutaneous route.

In alternative embodiments, the enzyme or an analog thereof is produced in vivo. In certain of these embodiments, the polypeptides so produced will then be isolated from the animal producing them (e.g., a transgenic animal into which the nucleic acid has been introduced). In other embodiments, the polypeptide will be produced by the cells of the patient, as will occur in gene therapy applications of the invention, wherein the nucleic acid molecule encoding *W. succinogenes* asparaginase or an analog thereof is delivered via a viral or non-viral gene delivery vehicle. Preferred viral gene delivery vehicles include recombinant retroviruses, alphaviruses, and adeno-associated viruses. Preferred non-viral systems include liposome- or polycation-associated nucleic acid constructs wherein the *W. succinogenes* asparaginase (or analog thereof) coding region is functionally associated with appropriate regulatory elements, which in some embodiments provide for tissue-specific expression.

A related aspect concerns nucleic acid molecules encoding *W. succinogenes* asparaginase analogs. Certain embodiments of this aspect are analogs which comprise at least one (in some embodiments, 2, 3, 4, 5, 6, 7, 8, 9, 10, or more) amino acid residue substitutions, deletions, and/or insertions, as compared to the amino acid sequence of the mature, native form of the enzyme. In some of these embodiments, the nucleic acid, in addition to coding for the respective amino acid alternation(s) which distinguish the enzyme as a *W. succinogenes* asparaginase analog, also includes one or more additional nucleotide substitutions which do not result in a change in the amino acid encoded by the codon(s) under consideration. Such conservative substitutions can serve to facilitate cloning (e.g., though introduction of a restriction endonuclease cleavage site) and/or optimize expression, for example, by including one or more codons preferred for expression in the particular host cell (i.e., those codons used in proteins expressed at high levels, as determined by statistical analysis of codons used in proteins which are expressed at high, moderate, or low levels in cells of the host) into which the nucleic acid is to be introduced. Such nucleic acid molecules are typically inserted, or cloned, into an expression vector capable of directing expression genes functionally inserted therein. In general, such vectors are plasmids which include a promoter (or other transcription activation sequence) at an appropriate distance from the 5'-terminus of the gene(s) to be expressed therefrom. In certain embodiments, the promoter is inducible. The expression vector also preferably encodes one or more selectable markers, which may or may not be separately regulated. In other embodiments, the vector is a component of a gene delivery vehicle. When the gene delivery vehicle is a virus, the vector typically comprises at least the components of the viral genome needed for gene expression and packaging into an infectious particle.

An additional aspect of the invention concerns derivatives of *W. succinogenes* asparaginase (derived from either a recombinant or natural source) and analogs thereof, and methods for producing the same. Such derivatives include those which been covalently modified to include a chemical moiety not found in the naturally occurring enzyme. Representative examples of such derivatives include those in which one or more amino acids have been glycosylated (as may occur when a recombinant form of the enzyme is produced in a host cell having the intracellular machinery required for protein glycosylation, e.g., a mammalian host cell), pegylated, acylated, or methylated. Recombinant forms of *W. succinogenes* asparaginase can be prepared as described above, although when a non-analog form is used for derivatization, the nucleic acid encoding the protein will code for a mature form of the native enzyme.

Yet another aspect of the invention relates to covalent modification of native and/or recombinant forms of *W. succinogenes* asparaginase. Certain embodiments of this aspect concern one or more covalent modifications to facilitate isolation/purification of recombinant forms of the enzyme. Other embodiments concern covalent modifications to alter substrate specificity, immuno-reactivity, biodistribution, serum half-life, etc.

Another aspect of the present is directed to methods for the therapeutic utilization of native and/or recombinant forms of *W. succinogenes* asparaginase in the treatment of diseases which respond to asparagine depletion, including certain neoplasias (e.g., acute lymphoblastic leukemia (ALL) and acute undifferentiated leukemia), as well as in the treatment of various non-malignant hematological and autoimmune diseases which respond to asparagine depletion. These methods involve administering to a patient a therapeutically effective amount of a *W. succinogenes* asparaginase, an analog thereof, or an acylated asparaginase derived from an organism other than *W. succinogenes*. Representative malignant diseases which can be so treated include certain hematologic diseases, for example, lymphomas, leukemias, and myelomas, including both chronic and acute phases. Representative non-malignant diseases which can be treated in accordance with the instant invention include autoimmune diseases, for example, arthritis (e.g., rheumatoid arthritis), SLE, and AIDS. Typically, the instant methods will be applied to humans afflicted with a disease which responds to asparagine depletion, although other patient classes, particularly mammals (e.g., bovine, canine, equine, feline, ovine, porcine, and primate animals) suffering from a disease which responds to asparagine depletion can be similarly treated.

Still other aspects of the invention concerns host cells containing nucleic acid molecules of the invention. For expression of *W. succinogenes* asparaginase and analogs thereof, microbial production systems are preferred, particularly bacterial, yeast, and mammalian cells systems. Another aspect relates to polypeptide derivatization methods using acylation. Preferred embodiments of this aspect relate to acylation of purified asparaginases, particularly *W. succinogenes* asparaginases (derived from both natural and recombinant sources) and analogs thereof. In a related aspect, methods are provided for altering a pharmacokinetic property of protein (e.g., asparaginase, particularly *W. succinogenes* asparaginase or an analog thereof) by acylating the protein.

Other features and advantages of the invention will be apparent from the following figures, detailed description, examples, and claims.

DESCRIPTION OF THE FIGURES

The present invention may be better-understood and its advantages appreciated by those individuals skilled in the relevant art by referring to the accompanying drawings wherein:

FIG. 1: illustrates the nucleotide sequences of the forward [SEQ ID NO. 1] and reverse [SEQ ID NO. 2] PCR primers used in the amplification of the genomic L-asparaginase sequences of *W. succinogenes*.

FIG. 6: illustrates the DNA sequence [SEQ ID NO. 3] of the modified *W. succinogenes* asparaginase-specific DNA insert. This sequence contains not only the coding sequence of the native *W. succinogenes* asparaginase (beginning with codon 40 of FIG. 6 and not including the final 23 3'-terminal nucleotides of FIG. 6), but also 39 codons for the N-terminal epitope "tag" shown in FIG. 6.

FIG. 7: is a schematic representation of a chemical modification for a protein, for example *W. succinogenes* asparaginase.

FIG. 8: illustrates the lack of cross-reactivity between different dilutions of a patient's plasma known to contain high-titer neutralizing antibodies against *E. coli* asparaginase and the *W. succinogenes* enzyme.

FIG. 9: illustrates the lack of cross-reactivity between different dilutions of polyclonal high-titer neutralizing antibodies against *E. coli* asparaginase and asparaginase derived from *W. succinogenes*.

DETAILED DESCRIPTION OF THE INVENTION

Figure 2:
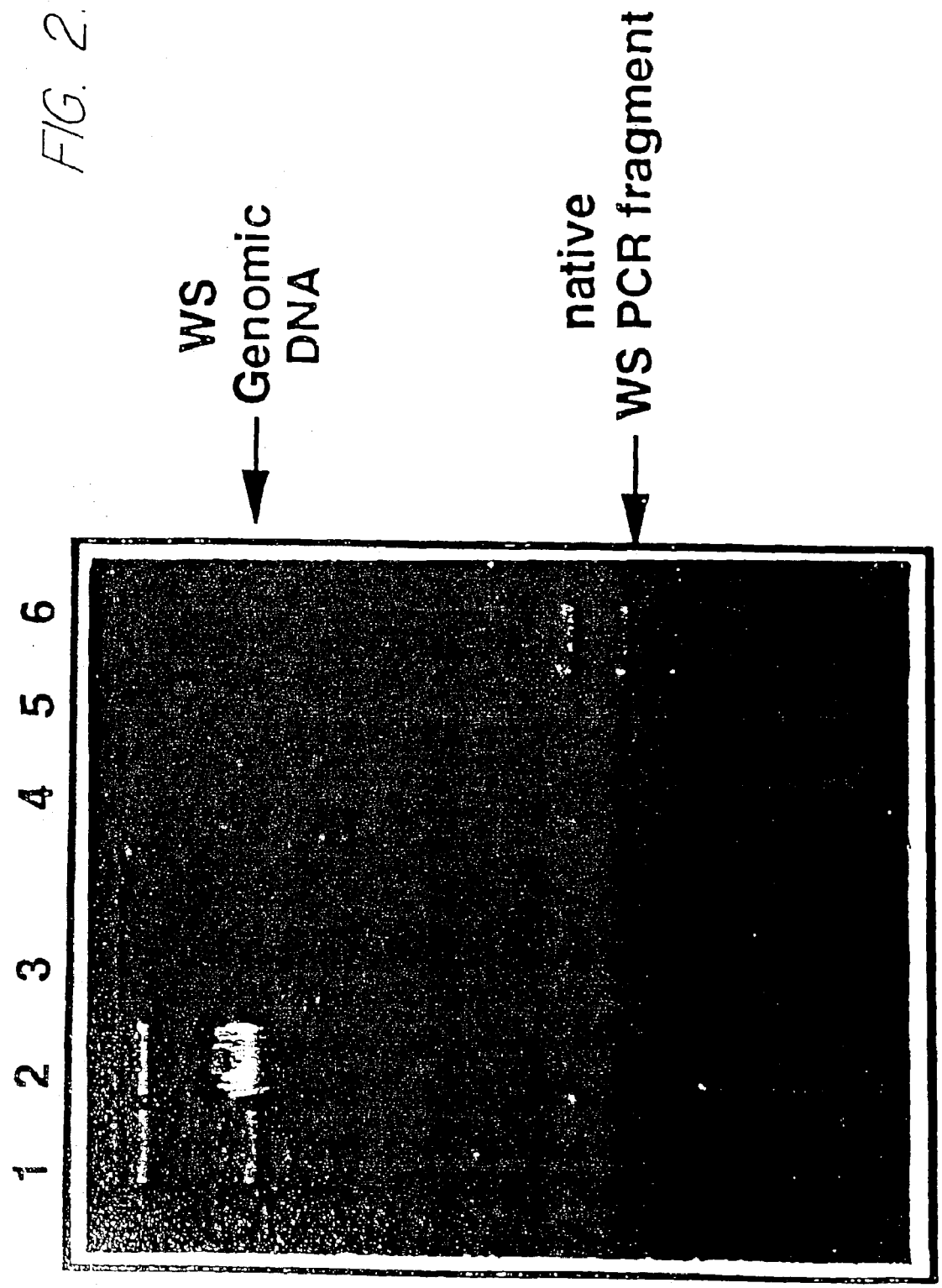
FIG. 2: Agarose gel electrophoresis of propidium iodine-stained *W. succinogenes* genomic DNA (lanes 1 and 2) and a 1.0 kb DNA fragment derived from PCR amplification. Lanes 3 and 4 are DNA molecular weight markers. Lane 5 is the 1.0 kb *W. succinogenes*-specific PCR fragment amplified using the two PCR primers shown in FIG. 1. Lane 6 contains φX174 DNA molecular weight marker.

This invention is based on the discovery that *W. succinogenes* asparaginase can be used an alternative form of asparaginase therapy in patients suffering from diseases which respond to asparagine depletion, particularly those who have been sensitized to other microbial enzymes by prior treatment. Furthermore, if required, patients initially treated with *W. succinogenes* asparaginase who subsequently develop hypersensitivity to this enzyme will likely be able to receive an immunologically distinct analog of *W. succinogenes* asparaginase or the *E. coli, E. carotovora,* or other covalently-modified asparaginases.

As discussed above, the clinical utilization of microbial asparaginases isolated from *E. coli, E. carotovora,* and PEG-modified *E. coli* asparaginase in the treatment of leukemia has previously been shown to result in a wide range of host toxicity (e.g., hepatic, renal, splenic, pancreatic dysfunction and blood coagulation), pronounced immunosuppression, and to elicit an allergic-type immunologic reaction with the concomitant formation of neutralizing antibodies, all of which serve to markedly decrease the therapeutic efficacy of these aforementioned microbial asparaginases.

Therefore, *W. succinogenes* asparaginase, particularly recombinant *W. succinogenes* asparaginase or an analog thereof, will provide patients with an alternative, immunologically distinct asparaginase and will allow most patients to complete the full-term course of asparaginase therapy, which is of paramount importance in the potential "cure" of their disease, e.g., leukemia. Moreover, the experimental data provided herein establishes that the recombinant form of the *W. succinogenes* asparaginase exhibits substantially similar, and perhaps identical, biochemical, pharmacological, and immunological properties as the native, homotetrameric form of the enzyme.

ADVANTAGES OF THE PRESENT INVENTION

As previously discussed, despite its therapeutic utility, microbial asparaginase therapy utilizing *E. coli,* PEG-modified *E. coli,* or *E. carotovora* asparaginases has numerous distinct clinical limitations, including: (1) hepatic, renal, pancreatic, CNS, and blood coagulation toxicity; (2) the causation of marked immunosuppression; and (3) eliciting an allergic reaction and the production of asparaginase-neutralizing antibodies. In contrast, these limitations in *W. succinogenes* asparaginase therapy are either greatly mitigated or non-existent, therefore making this enzyme highly efficacious in, for example, the treatment of malignant hematologic diseases and other conditions associated with asparagine dependence.

Described herein are methodologies for the isolation of the "native," homotetrameric *W. succinogenes* asparaginase which possesses potent anti-neoplastic activities, and for the production (using recombinant expression vectors) of rWS and analogs thereof, e.g., those which have been acylated and those which have been modified to include additional or alternate amino acids that have been acylated or otherwise modified (e.g., by pegylation). In certain preferred embodiments, the rWS enzyme is a recombinant form of the native, homotetrameric asparaginase from *W. succinogenes* (previously *V. succinogenes;* see Durden, D. L., A glutaminase-free asparaginase from *Vibrio succinogenes* lacking immunosuppression and toxicity, *Ph. D. Dissertation,* University of Miami Medical School (1983); Durden, D. L. & Distasio, J. A., Characterization of the effects of asparaginase from *E. coli* and a asparaginase from *Vibrio succinogenes,* 40 *Cancer Res.* 1125 (1980)).

The nucleotide sequence encoding the gene for *W. succinogenes* was determined in 1995, in addition to several hundred bases of 5' and 3' flanking regions (see GenBank accession number X89215). The amino acid sequence and three-dimensional structure of the enzyme has also been described. See Lubkowski, et al., *Eur. J. Biochem.,* vol. 241:201–207 (1996).

As previously discussed, *W. succinogenes* asparaginase has been shown to be immunologically distinct from the *E. coli* enzyme (see Distasio, J. A. & Niederman, T. (1976), supra). Moreover, previous results have established that *W. succinogenes* asparaginase does not suppress either the humoral or cell-mediated immunological response to the T cell-dependent antigen, SRBC, even when administered in dosages 5-fold higher than the levels of the *E. coli* enzyme which are capable of completely abrogating these responses (see Durden, D. L. & Distasio, J. A., Characterization of the effects of asparaginases from *Escherichia coli* and a asparaginase from *Vibrio succinogenes* on specific cell-mediated cytotoxicity, 27 *Int. J. Cancer* 59 (1981); Durden, D. L. & Distasio, J. A. (1980), supra).

The following sections elaborate upon some of the various biochemical and physiological effects of clinical utilization of asparaginase therapy in the treatment of malignant diseases associated with asparagine dependence, particularly hematologic disease.

1. Effects of Asparaginase Treatment on Spleen and Thymus Histology and Lymphocyte Population.

Examination of the effects of *E. coli* asparaginase treatment on spleen histology and lymphocyte populations are known to cause a marked reduction in both the size and reactivity of the splenic germinal centers, which changes are concomitantly associated with a marked reduction in the cytoplasmic immunoglobulin-containing cells (B-cell immunoblasts; see Distasio, J. A., et al. (1982), supra). Additionally, it is known that spleen lymphocyte subpopulations show up to a 40% reduction in the percentage of surface immunoglobulin-expressing cells (B-cells) accompanied by an increase in the ratio of Thy-1,2-expressing cells (T-cells), whereas the ratio of Lyt-2 to Lyt-1 cells remains unchanged. In contrast, asparagine deprivation alone, caused by the administration of *W. succinogenes* asparaginase, has no demonstrable effect on spleen histology or lymphocyte marker distribution.

Similarly, histological examination of the thymus following *E. coli* asparaginase administration revealed a pronounced depletion of cortical thymocytes, whereas no changes in thymus histology or cellularity were found after *W. succinogenes* asparaginase administration. Therefore, a comparison of the effects of long-term administration on spleen and thymus histology, cellularity, and weight indicated that *E. coli* asparaginase treatment was associated with a pronounced, sustained reduction in these parameters in both the spleen and thymus.

II. Hepatic Toxicity Associated with Asparaginase Administration

Hepatotoxicity is the major clinical toxicity associated with the therapeutic administration of both *E. coli* and *E. carotovora* asparaginases (see Broome, J. D., Factors which may influence the effectiveness of L-asparaginase as tumor inhibitors, 22 *Br. J. Cancer* 595 (1969)). The hepatotoxic effects of these two microbial enzymes was compared with those associated with the administration of *W. succinogenes* asparaginase (see Durden, D. L., et al., Kinetic analysis of hepatotoxicity associated with anti-neoplastic asparaginases, 43 *Cancer Res.* 1602 (1983); Distasio, J. A., et al., Glutaminase-free asparaginase from *Vibrio succinogenes:* an anti-lymphoma enzyme lacking hepatotoxicity, 30 *Int. J. Cancer* 343 (1982)).

Administration of 50 IU of *E. coli* asparaginase to Balb/c mice for 4 days resulted in a diffuse, microfatty infiltration of hepatocytes throughout the liver. In contrast, microscopic examination of cross sections from Balb/c mice treated with *W. succinogenes* asparaginase displayed identical hepatic histology to that of the control animal group. Quantitation of the total amount of extractable lipid from the livers of *E. coli* asparaginase-treated Balb/c mice indicated a 45% and 127% increase in lipid concentration, as compared to the control animal group after 4 and 5 days of treatment, respectively. Administration of *W. succinogenes* asparaginase caused no quantitative change in the total amount of extractable hepatic lipid as compared to the control animal group. In addition, plasma concentration of albumin, triglyceride, and cholesterol, as well as anti-thrombin III activity all were shown to be decreased in Balb/c mice as a result of *E. coli* asparaginase administration, thus confirming hepatotoxicity. The plasma levels of anti-thrombin III were found to be unchanged by administration of *W. succinogenes* asparaginase, and while plasma lipid concentrations were found to be minimally decreased, only the levels of cholesterol were shown to be altered in a statistically way significant from the levels exhibited by the control animals.

In addition, the observed hepatotoxic effects of long-term administration of *E. coli* and *E. carotovora* asparaginases were compared to those of *W. succinogenes* asparaginase. Results obtained from the Balb/c murine model demonstrated that hepatotoxicity associated with the administration of *E. coli* asparaginase paralleled the hepatotoxicity observed in humans, with a rapid increase in total extractable hepatic lipid levels and concomitant decreased plasma levels of albumin, triglyceride, and cholesterol, as well as anti-thrombin III activity occurring in the first and second weeks of treatment, followed by a resumption to normal hepatic function during weeks 3 and 4. Administration of *E. carotovora* asparaginase was associated with an intermediate level of hepatotoxicity, with increased total extractable hepatic lipid concentration occurring during the second and fourth week of treatment. Conversely, prolonged treatment of Balb/c mice with *W. succinogenes* asparaginase was not found to be associated with any demonstrable hepatotoxicity. These results from long-term administration suggest that the observed hepatotoxicity may be a direct result of the combined physiological depletion of asparagine and glutamine.

III. Anti-Neoplastic Activity Associated with Asparaginase Administration

Figure 5:
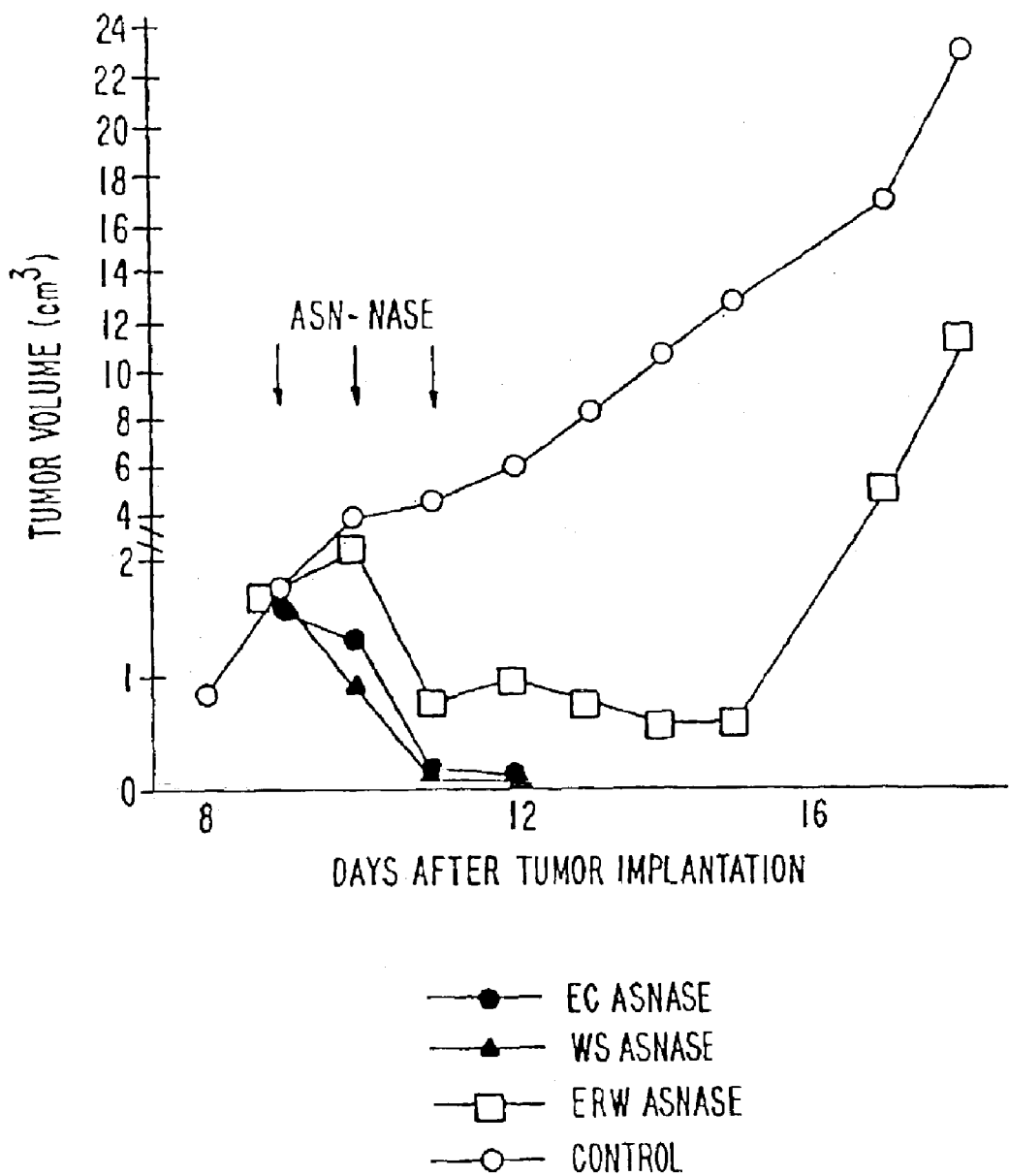
FIG. 5: illustrates the results of a determination of the anti-tumor activity of *W. succinogenes* (WS), *E. coli* (EC) and *E. carotovora* (Erw) asparaginases against tumors generated by the subcutaneous injection of 6C3HED Gardner lymphosarcoma cells in C3H mice. Anti-tumor activity was measured as a function of caliper-measured tumor volume ($cm^3$). The negative control consisted of injections of 0.01 M phosphate buffer (pH 7.0) into C3H mice using the same injection schedule as for the asparaginases.

The relative anti-neoplastic (anti-lymphoma) activity of native, homotetrameric *E. coli*, *E. carotovora*, and *W. succinogenes* asparaginases were determined against 6C3HED Gardener's lymphosarcoma which had been previously implanted in C3H mice. The results of this study are illustrated in FIG. 5. The control group of animals receiving only 0.01 M phosphate buffer all died within 20 days following initial tumor implantation.

Administration of either *E. coli* or *W. succinogenes* asparaginase resulted in complete remission of the lymphosarcoma in 100% of the animals. The animals were examined for 60 to 90 days following initial tumor implantation with no evidence of tumor. Similarly, animals followed for longer periods of time demonstrated normal longevity with no recurrence of tumor. However, as previously discussed, the utilization of *E. coli* asparaginase is associated with both toxicity and immunosuppression which markedly limits its ability to be used in the treatment of neoplastic disease.

Administration of *E. carotovora* asparaginase resulted in initial regression, followed by a rapid tumor proliferative phase. All animals died (100% mortality) from the development of lymphosarcoma within 30 days post-tumor implantation. Similar results were obtained using the P1798 lymphosarcoma tumor in Balb/c mice.

IV. Immune Cross-Reactivity of Asparaginases

As previously discussed, patients treated with *E. coli* and *E. carotovora* asparaginases frequently develop immunologic delayed-type hypersensitivity reactions with the concomitant production of neutralizing antibodies directed against the specific asparaginase enzyme. Moreover, with the use *E. coli* asparaginase in the treatment of childhood acute lymphoblastic leukemia (ALL), these aforementioned phenomenon have resulted in a loss of the efficacy of the drug/enzyme and, in some cases, to a recurrence of the leukemia. This immunoreactivity has led to the search for methods to decrease the immunogenicity of asparaginases and to develop other non-cross-reactive forms of this enzyme for clinical use.

Studies have demonstrated that the native, homotetrameric form of *W. succinogenes* asparaginase does not cross-react immunologically with either the *E. coli* (EC) or *E. carotovora* (Erw) asparaginases (see Distasio, J. & Niedennan, A., Purification and characterization of L-asparaginase with anti-lymphoma activity from *Vibrio succinogenes*, 251 *J Biol. Chem.* 6929 (1976)). Herein, experiments are described herein to evaluate the immunological cross-reactivity of both the native, homotetrameric (WS) and recombinant (rWS) forms of *W. succinogenes* asparaginase using the serum or plasma from patients known to have developed neutralizing antibodies against the EC or Erw asparaginases. In addition, the capacity of the serum or plasma of patients (who have been previously shown to be allergic to EC asparaginase) to cross-react with EC, Erw, WS, and rWS asparaginases has been assessed using a double immunodiffusion assay system. Recent studies suggest that the subclinical detection of anti-EC asparaginase antibodies in patients treated with the EC-derived enzyme is associated with a loss efficacy of the EC and PEG-asparaginases in vivo (see Avramis, V. & Periclou, I. (1997), supra).

The experimental results described herein demonstrates that it is highly probable that antibodies made in response to xenoimmunization in humans and rabbits to both EC and Erw asparaginase will not cross-react with either WS or rWS asparaginase, nor will they neutralize the enzymatic activity of either form of the enzyme in vivo or in vitro. Similarly, these results also serve to establish that antibodies directed against EC or PEG asparaginase in humans will not cross-react or neutralize WS or rWS asparaginase. Together, these data have provided for developing a rationale for an efficacious clinical application of WS and rWS asparaginase (or analogs thereof) in patients who have previously developed an immunologic-based hypersensitivity to the EC and/or PEG asparaginases.

In addition, due to intrinsic immunosuppressive and anti-metabolic activities, WS and/or rWS asparaginase (or analogs thereof), may also, be utilized in the therapeutic treatment of various autoimmune diseases such as rheumatoid arthritis, systemic lupus erythematosis, AIDS, etc. Although WS asparaginase has less immunosuppressive activity than that of EC asparaginase, the lower level of associated host toxicity makes it ideal for clinical utilization in non-malignant diseases which respond to asparagine depletion.

Covalent Modification of Asparaginases and Other Proteins

Many proteins currently used to treat human diseases have extremely short circulating half-lives which limit their efficacy. In addition, the administration of many foreign proteins (including certain recombinant proteins) is associated with allergic hypersensitivity responses which can also lead to the production of neutralizing antibodies which hasten the rapid elimination of these therapeutic proteins from plasma. To overcome these and other problems, the invention provides a covalent modification procedure to chemically modify proteins, including asparaginases, particularly *W. succinogenes* asparaginase, in order to extend their half-lives, reduce their immunogenicity, and increase their efficacy. This chemical modification regimen involves the systematic alteration of protein structures by conjugating an aliphatic hydrocarbon chain (be saturated, partially saturated, or unsaturated, a straight chain, a branched chain, and/or a chain of aromatic) of an acylating agent to polar groups within the protein structure (see FIG. 7). While this process is generally applicable to any protein to be introduced into a patient, below conditions are described for covalently modifying *E. coli* and *W. succinogenes* asparaginase using an acid chloride.

Compositions, Formulation, and Administration

As described above, *W. succinogenes* asparaginase (and its analogs and derivatives) can be used to treat diseases which respond to asparaginase depletion. These compounds may also be used to treat such diseases prophylactically, or to treat those patients previously diagnosed with and treated for such a disease. For example, a patient previously diagnosed and successfully treated for leukemia, or whose disease is otherwise in remission, may experience a relapse. Such patients may also be treated in accordance with the claimed invention.

*W. succinogenes* asparaginase, and its biologically active analogs and derivatives, as well as other acylated asparaginases and proteins, can be administered to a patient using standard techniques. Techniques and formulations generally may be found in *Remington's Pharmaceutical Sciences*, 18$^{th}$ ed., Mack Publishing Co., Easton, Pa., 1990 (hereby incorporated by reference).

Suitable dosage forms, in part, depend upon the use or the route of entry, for example, oral, transdermal, transmucosal, or by injection (parenteral). Such dosage forms should allow the therapeutic agent to reach a target cell or otherwise have the desired therapeutic effect. For example, pharmaceutical compositions injected into the blood stream preferably are soluble.

Pharmaceutical compositions according to the invention can be formulated as pharmaceutically acceptable salts and complexes thereof. Pharmaceutically acceptable salts are non-toxic salts present in the amounts and concentrations at which they are administered. The preparation of such salts can facilitate pharmaceutical use by altering the physical characteristics of the compound without preventing it from exerting its physiological effect. Useful alterations in physical properties include lowering the melting point to facilitate transmucosal administration and increasing solubility to facilitate administering higher concentrations of the drug. The pharmaceutically acceptable salt of an asparaginase may be present as a complex, as those in the art will appreciate.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate, and quinate. Pharmaceutically acceptable salts can be obtained from acids, including hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences, supra*. Such salts can be prepared using the appropriate corresponding bases.

Pharmaceutically acceptable carriers and/or excipients can also be incorporated into a pharmaceutical composition according to the invention to facilitate administration of the particular asparaginase. Examples of carriers suitable for use in the practice of the invention include calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include sterile solutions of water for injection (WFI), saline solution and dextrose.

Pharmaceutical compositions according to the invention can be administered by different routes, including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous injection. For injection, pharmaceutical compositions are formulated in liquid solutions, preferably in physiologically compatible buffers or solutions, such as saline solution, Hank's solution, or Ringer's solution. In addition, the compounds may be formulated in solid form and redissolved or suspended immediately prior to use. For example, lyophilized forms of the asparaginase can be produced.

Systemic administration can also be accomplished by transmucosal or transdermal means. For transmucosal or transdermal administration, penetrants appropriate to the barrier to be permeated are used in the formulation. Such penetrants are well known in the art, and include, for example, for transmucosal administration, bile salts, and fusidic acid derivatives. In addition, detergents may be used to facilitate permeation. Transmucosal administration, for example, may be through nasal sprays, inhalers (for pulmonary delivery), rectal suppositories, or vaginal suppositories. For topical administration, compounds can be formulated into ointments, salves, gels, or creams, as is well known in the art.

The amounts of the active therapeutic agent to be delivered will depend on many factors, including the particular therapeutic agent, for example, *W. succinogenes* asparaginase, the agent's $IC_{50}$, $EC_{50}$, the biological half-life of the compound, the age, size, weight, and physical condition of the patient, and the disease or disorder to be treated. The importance of these and other factors to be considered are well known to those of ordinary skill in the art. Generally, the amount of asparaginase to be administered will range from about 10 International Units per square meter of the surface area of the patient's body ($IU/M^2$) to 50,000 $IU/M^2$, with a dosage range of about 1,000 $IU/M^2$ to about 15,000 $IU/M^2$ being preferred, and a range of about 6,000 $IU/M^2$ to about 10,000 $IU/M^2$ being particularly preferred to treat a malignant hematologic disease, e.g., leukemia. Typically, these dosages are administered via intramuscular or intravenous injection three times per week, e.g. Monday, Wednesday, and Friday, during the course of therapy. Of course, other dosages and/or treatment regimens may be employed, as determined by the attending physician.

In addition to administering a *W. succinogenes* asparaginase enzyme to treat a disease which responds to asparagine depletion, other embodiments of the invention concern administration of a nucleic acid construct encoding the enzyme or an analog thereof. As those in the art will appreciate, a variety of different gene delivery vehicles (GDVs) may be employed for this purpose. GDVs include viral and non-viral delivery systems. Representative viral delivery systems include recombinant retroviral vectors which provide for stable, long term, and generally low level expression of one or more heterologous genes via integration in the genome of cells transfected by the virus. Here, retroviral GDVs will encode *W. succinogenes* asparaginase or an analog thereof, and may also include one or more other heterologous genes, for example, a gene encoding a conditionally lethal gene (e.g., thymidine kinase, which converts the pro-drug gancyclovir to its cytotoxic form) to eliminate the transfected cells, if desired.

Other viral delivery systems include those based on adeno-associated virus (AAV) and various alpha viruses, e.g., Sindbis and Venezuelan equine encephalitis virus. These other viral GDVs may provide for higher level expression, or expression for different duration, of the desired heterologous gene(s). As those in the art will appreciate, the host range for the particular virus employed may be altered by techniques well known in the art.

Non-viral GDVs useful in the practice of these embodiments of the invention include, among others, so-called "naked DNA" systems which provide the desired heterologous gene(s) in functional association with an appropriate promoter (which in certain embodiments may be an inducible or tissue-specific promoter) encoded by the nucleic acid construct. Other regulatory elements may also be included, for example, enhancers and other activators of gene expression. Preferably, such non-viral systems are incorporated into liposomes or are associated with polycationic reagents to facilitate introduction of the nucleic acid construct into cells of the patient. Of course, other components can also be included in such GDVs, e.g., molecules to target one or more particular cell types, fusogenic peptides to facilitate endocytotic vesicle escape, etc. Construction of these and other GDVs useful in the practice of this invention are within the skill of those in the art.

EXPERIMENTAL METHODOLOGIES AND RESULTS

The following examples will serve to further illustrate various aspects of the present invention and are not intended to act in any manner as limitations on the claimed invention. In addition, methodologies are provided which will permit one of ordinary skill within the relevant arts to determine whether a derivative asparaginase is appropriate for utilization in the clinical therapeutic treatment of humans. For a discussion of molecular biology techniques which can be used in the practice of this invention, in addition to those described below, see *Molecular Cloning, A Laboratory Manual,* 2d ed., ed. Sambrook, et al., Cold Spring Harbor Laboratory Press, 1989, and *Current Protocols In Molecular Biology,* ed. Ausubel, et al., John Wiley & Sons, Inc., 1995.

EXAMPLE 1

In Vitro Culture of *W. succinogenes*

*W. succinogenes* was grown in 10–15 liters of liquid culture media containing 0.4% yeast extract, 100 mM ammonium formate, and 120 mM sodium fumerate. The medium was adjusted to pH 7.2 prior to autoclaving. After autoclaving, a 0.2 μm filter-sterilized solution of thioglycolate was added to the room temperature culture medium to give a final concentration of 0.05%. The cultures were incubated with continuous agitation on a shaking platform in a 37° C. warm-room. For large scale culture, a 500 ml pre-culture was utilized to inoculate 10–15 liters of complete culture medium.

The bacteria were collected after the cultures had reached a optical density of approximately 1.1 at a 650 nm wavelength, by centrifugation using a Sorvall high-speed continuous flow rotor. Following centrifugation, the cells were washed in a buffer containing 0.15 M sodium chloride, 0.1 M magnesium chloride, and 0.01 M mercaptoethanol. The cells were then resuspended in 0.1 M borate buffer (pH 9.0) at a final concentration of 0.5 g wet cell weight/ml borate buffer and stored frozen until subsequent processing for enzyme purification.

EXAMPLE 2

Animals and Cell Lines

The murine model animals utilized in these experiments were Balb/c or C3H mice of 9 to 12 weeks in age (Jackson Laboratories, Bar Harbor, Me.).

The therapeutic activity of L-asparaginases was determined utilizing the 6C3HED Gardner's lymphosarcoma (Gardner, W. U., *Cancer Res., vol.* 4: 73 (1944)) and P1798 lymphosarcoma cell lines (ATCC) which as ascites tumors in C3H and Balb/cc mice, respectively. Alternately, the two lymphosarcoma cell lines were cultured in RPMI 1640 medium supplemented with 10% fetal calf serum. The 6C3HED Gardner's lymphosarcoma originated in the thymus of C3H mice which were initially given high doses of estradiol. The lymphosarcoma was subsequently perpetuated by serial transplantation in the C3H mice.

EXAMPLE 3

Isolation of *W. succinogenes* Genomic DNA

Genomic DNA from *W. succinogenes* was extracted from bacteria grown in basal medium. Typically, bacterial cells from a 50 ml of culture were collected by centrifugation and resuspended by gentle vortexing in 1.5 ml TE buffer (pH 7.0). To the cell suspension was added 15 μl of 10% SDS to give a final concentration of 0.1% and 3 μl of a 20 mg/ml stock solution of proteinase K. The mixture was then incubated at 37° C. for approximately 60 minutes, followed by several phenol/chloroform extractions. The genomic DNA was ethanol precipitated and collected by centrifugation. The *W. succinogenes* genomic DNA so isolated was sufficiently pure to use in high stringency PCR amplification.

EXAMPLE 4

Amplification of *W. succinogenes* Asparaginase Sequences

The nucleotide sequence of a 2.5 kb Hind III fragment containing the 993 nucleotide coding region of *W. succinogenes* asparaginase was published in 1995. See GenBank accession number X89215. The elucidation of this sequence facilitated the synthesis of primers specific for PCR amplification of the gene coding, for the *W. succinogenes* enzyme. As illustrated in FIG. 1, the forward and reverse *W. succinogenes* asparaginase-specific PCR primers forward and reverse had the following sequences:

5'-TCCGGATCCAGCGCCTCTGTTTTGATGGCT-3' Forward PCR Primer [SEQ ID NO. 1]
(BamH1] Restriction Site Underlined)
5'-TGGGAATTCGGTGGAGAAGATCTTTTGGAT-3' Reverse PCR Primer [SEQ ID NO. 2]
(EcoR1 Site Restriction Underlined)

It should be noted that the genomic *W. succinogenes* asparaginase coding sequence does not naturally contain either a BamH1 or EcoR1 restriction site. However, PCR amplification utilizing these aforementioned primers introduced a BamH1 and EcoR1 restriction site to the 5'- and 3'-termini, respectively to facilitate directional cloning of this amplified genomic sequence into sequencing and/or expression vectors.

With respect to PCR amplification, *W. succinogenes* genomic DNA (purified as per Example 3) was subjected to 30 cycles of PCR amplification under the following reaction conditions: 10 µl PCR II reaction buffer; 6 µl of 25 mg/ml magnesium chloride, 8 µl of 10 mM stock solutions of dNTPs, 1 µl of Taq DNA polymerase (Stratagene Corp.); 1 µl (about 50 ng) each of the *W. succinogenes* asparaginase-specific forward and reverse PCR primers; 1 µl of *W. succinogenes* genomic DNA; and nuclease-free PCR-grade water to bring the reaction mixture to 100 µl total volume. Following amplification, 2 µl of the PCR products were electrophoresed through a 1% agarose gel and stained with propidium iodine to assess both the specificity of the amplification reaction and the molecular weight of the resulting DNA fragments. The amplification resulted in the production of a homogeneous, 1.0 kb *W. succinogenes* asparaginase-specific DNA fragment.

EXAMPLE 5

Cloning of *W. succinogenes* Asparaginase Sequences

The amplified *W. succinogenes* asparaginase-specific amplified DNA fragment was subsequently sub-cloned into the BamH1 and EcoR1 sites of the PCRII cloning vector (Stratagene, La Jolla, Calif.) utilizing the following reaction conditions: 2 µl of the PCR amplified reaction products, 2 µl of the PCRII cloning vector; 1 µl of 10X ligation buffer; 4 µl of T$_4$ DNA ligase (Stratagene, La Jolla, Calif.); and distilled/deionized water to bring the total reaction volume to 10 µl. The ligation reaction was incubated at 16° C. overnight and 2 µl of this reaction was utilized to transform competent *E. coli* strains DH-5α and M15.

IPTG-induced colorimetric selection (medicated by expression of β-galactosidase in the presence of X-GAL) was utilized to identify recombinant bacterial colonies. Three white colonies (putative positive recombinants) and one blue colony (putative negative recombinants) were chosen, inoculated into a 5 ml culture of LB medium containing 100 µg/ml ampicillin, and incubated overnight at 37° C. on a shaking platform. Plasmid DNA was isolated from these cultures via standard DNA "mini-prep" methodology and the DNA was dissolved in 30 µl TE buffer and digested with 3 different restriction endonucleases: BamH1; EcoR1; and BamH1/EcoR1, to ensure that the isolated plasmid DNA contained the expected 1.0 kb *W. succinogenes* asparaginase-specific insert.

Figure 3:
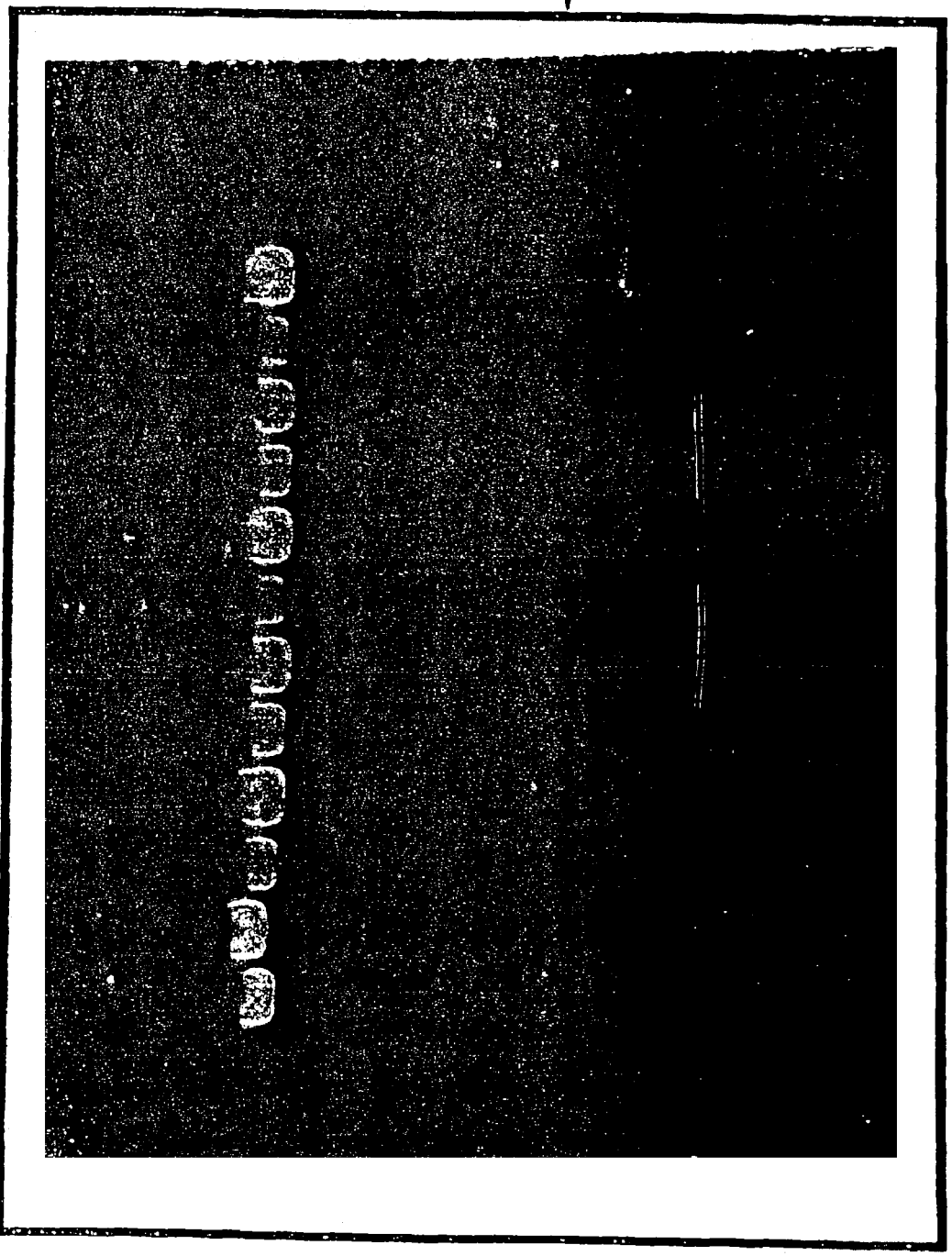
FIG. 3: Restriction enzyme analysis of 4 colonies which were isolated following the ligation of the 1.0 kb *W. succinogenes*-specific PCR fragment into the PCR II vector. The 1.0 kb DNA was digested with BamHI (lanes 2–5); EcoRI (lanes 6–9); and BamH1 and EcoR1 (lanes 10–13). Lane 14 represents a DNA molecular weight ladder. The 1.0 kb *W. succinogenes*-specific DNA fragment is denoted by an arrow.
Figure 4:
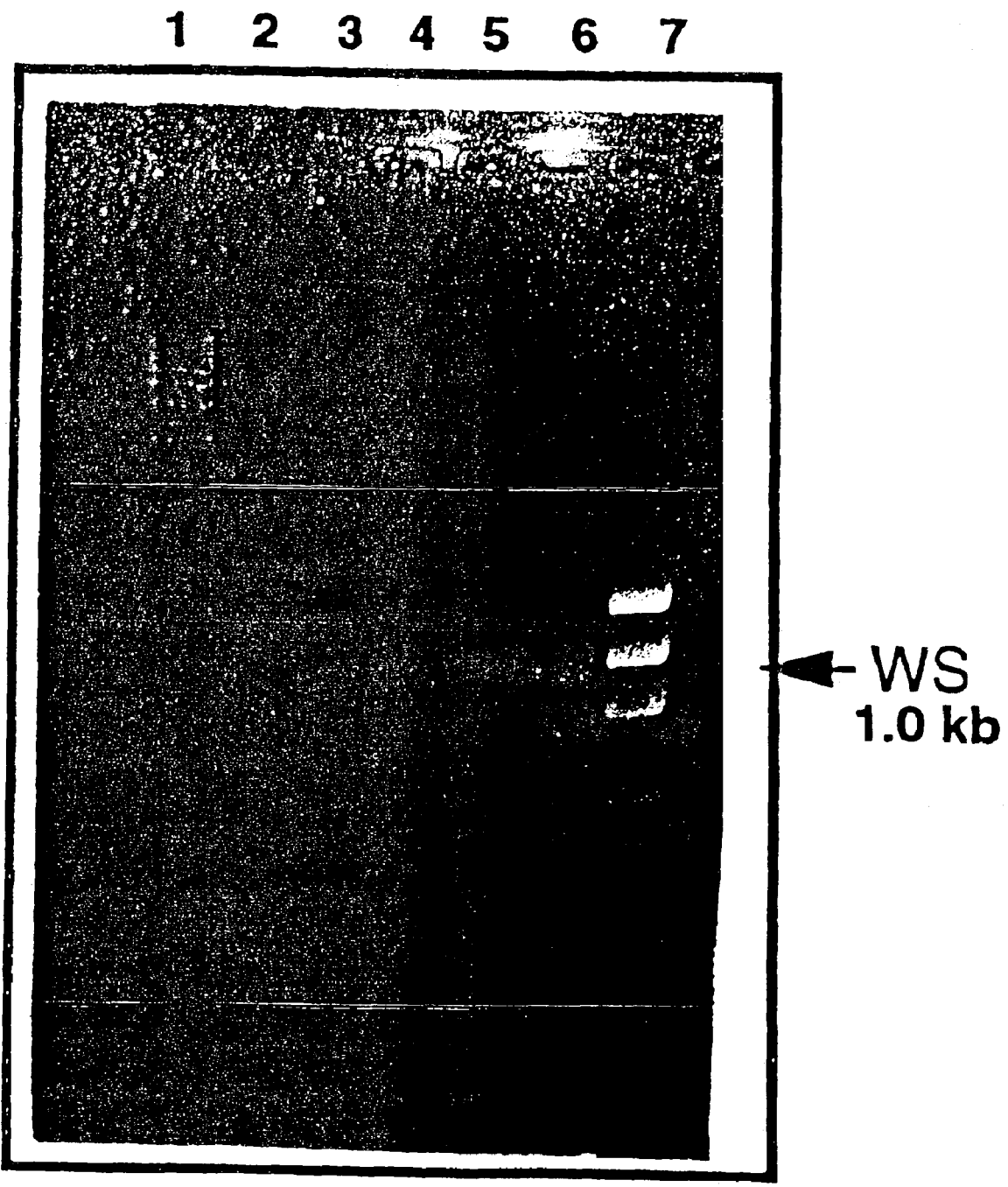
FIG. 4: Agarose gel electrophoresis of the DNA fragments amplified from the selected, "positive" clones utilizing *W. succinogenes* asparaginase-specific primers. Lanes 1 and 7 are molecular weight markers. Lanes 2 and 4 represent DNA extracted from bacterial colonies #1 and #3 from lanes 2 and 4 of FIG. 3. Lane 6 represents a sample of the *W. succinogenes* asparaginase PCR amplification product (amplified from *W. succinogenes* genomic DNA from FIG. 2, lane 5) used in the initial ligation reaction. It should be noted that the fragment cloned into the PCR II vector was shown to be exactly the same size (e.g., 1.0 b) as the initial PCR amplification product.

The electrophoretic results, as illustrated in FIG. 3, lanes 2 and 4, demonstrated that colonies #1 and #3 contained the expected 1.0 kb insert. To confirm that these clones contained the *W. succinogenes* asparaginase gene, the *W. succinogenes* asparaginase-specific PCR primers were used to amplify the *W. succinogenes* asparaginase-specific fragments isolated from the aforementioned clones (FIG. 3, lanes 2 and 4). These primers did not mediate amplification of non-insert-containing bacterial DNA (FIG. 3, lane 3). Results of this second PCR amplification demonstrated that colonies #1 and #3 contained the *W. succinogenes* asparaginase-specific DNA insert within the PCRII cloning vector, resulting in the generation of a 1.0 kb amplification product (see FIG. 3, lanes 2 and 4).

The *W. succinogenes* asparaginase-specific DNA insert in the PCR II cloning vector was then removed by BamH1 and EcoR1 digestion of 10 g of plasmid DNA derived from colony #1, gel-purified via the use of Gene Clean Kit® (Stratagene, La Jolla, Calif.). The DNA insert was eluted from the gel with 10 µl distilled/deionized water and then ligated overnight at 16° C. into the similarly restricted pGEX-2T (Amersham Pharmacia Biotech, Piscataway, N.J.) and pET-28a (Novagen, Inc., Madison, Wis.) vectors under the following reaction conditions: 3 µl DNA insert; 3 µl vector DNA; 4 µl 5X ligation reaction buffer; 1 µl T$_4$ DNA ligase; and 9 µl of distilled/deionized water to give a final reaction volume of 20 µl. 10 µl of each ligation reaction mixture was used to transform 50 µl of competent *E. coli* DH-5α cells. Transformants were then plated onto LB agar plates containing 100 mg/ml ampicillin. Positive transformants (i.e., *W. succinogenes* asparaginase-specific DNA insert-containing transformants, pGEX-2T-WSA and pET-28-WSA, respectively) were obtained following approximately 18 hours of incubation at 37° C. To confirm that the transformants contained the *W. succinogenes* asparaginase-specific DNA insert, restriction endonuclease digestion using BamH1 and EcoR1 was performed, as well as PCR amplification and DNA sequence analysis. Results of these analyses demonstrated that each of the selected "positive" transformants contained the *W. succinogenes* asparaginase-specific DNA insert. The nucleotide sequence of the *W. succinogenes* asparaginase-specific DNA insert is shown in FIG. 6 [SEQ ID NO. 3], which sequence contains 117 nucleotides 5' to the initial codes of the *Wolinella* gene and 23 nucleotides 3' to the gene's termination codon.

EXAMPLE 6

Expression of Recombinant *W. succinogenes* Asparaginase Analogs

To facilitate isolation of the recombinant *W. succinogenes* (rWS) asparaginase protein, several types of epitope-labeled asparaginase analogs have been constructed. These epitope labels included: influenza hemagglutinin (HA); glutathione-S-transferase (GST); DYLD (FLAG); and poly-histidine (p-His). In each instance, the label is placed on the N-terminus of the enzyme.

The following methodologies are utilized to isolate these various epitope labeled rWS asparaginase proteins:

(1) GST-sepharose (Pharmacia AB, Upsala, Sweden) column chromatography is utilized to purify the GST-labeled rWS asparaginase enzyme expressed from the pGEX-2T-WSA vector, followed by cleavage by thrombin.

(2) Protein-G-sepharose immobilized anti-HA and anti-FLAG antibodies (Pharmacia AB, Upsala, Sweden) is utilized to affinity purify the HA-or FLAG-labeled rWS asparaginase enzyme.

(3) Nickel resin (Ni-NTA [nitrilo-tri-acetic acid resin]; Novagen, Inc., Chatsworth, Calif.) is used to affinity purify p-His-labeled rWS asparaginase enzyme.

More specifically, for example, production of polyhistidine (p-His)-labeled, glutathione-S-transferase (GST)-rWS asparaginase requires the induction of positively transformed *E. coli* with IPTG, followed by harvesting of the bacteria (see Hochuli, E., & Dobell, N, New metal chelate absorbents selective for protein and peptide containing neighboring histidine residues, 411 *J. Chromatography* 177 (1987)). In such expression systems, vectors such as pGEX-2T and pET-28a expression vectors may be utilized to facilitate the expression of a non-epitope-labeled form of the rWS asparaginase following IPTG induction. The p-His-labeled constructs, localized in the N-terminus of the rWS asparaginase, can then be sub-cloned into the BamH1 to EcoR1 site of the pET-28a vector (Novagen, Inc., Chatsworth, Calif.) for expression of the p-His-labeled rWS enzyme.

EXAMPLE 7

Purification of Native *Wolinelia succinogenes* Asparaginase

The native, homotetrameric form of *W. succinogenes* asparaginase was purified according to the following methodology. *W. succinogenes* cell lysates were prepared by subjecting bacteria cultured and frozen in accordance with Example 1 to 3 to 4 freeze/thaw cycles with sonication, followed by high-speed centrifugation to remove cell debris. After centrifugation, the supernatant was brought to 0.1 M concentration of ammonium sulfate at a temperature of 4° C. The mixture was then brought to a final volume of 120% by the addition of a 2% protamine solution, followed by centrifugation for 30 min. at 21,000×g. The supernatants were recovered, pooled, and brought to a 50% ammonium sulfate saturation and equilibrated for 30 minutes on ice with continuous stirring. The resulting solution was then dialyzed against 0.01 M potassium phosphate buffer (pH 8.0) and applied to a 3 cm×20 cm hydroxyapatite column (prepared by: Pharmacia, Inc.) equilibrated with 0.1 M potassium phosphate buffer pH 8.0.

The *W. succinogenes* asparaginase was eluted from the hydroxyapatite column utilizing step-wise concentrations of phosphate buffer (i.e., 0.10, 0.20, 0.25, 0.30, 0.35 M phosphate buffer, pH 8.0). The eluted fractions (10 mL/fraction) were collected, assayed for asparaginase enzymatic activity, and pooled. The enzymatically-active fractions were dialyzed against 0.1 M sodium borate buffer (pH 7.0) and applied to a 3 cm×20 cm DEAE-Sephadex column (prepared by Pharmacia, Inc.) equilibrated in 0.1 M sodium borate buffer, pH 7.0. The enzyme was eluted by use of a linear gradient of sodium chloride (0 to 1.0 M) in 0.1 M sodium borate buffer (pH 7.0). 60 mL asparaginase-containing fractions were retained. *W. succinogenes* L-asparaginase prepared utilizing this methodology has been shown to be homogeneous by SDS-PAGE electrophoresis and silver staining.

*E. coli* EC-2 asparaginase (Merci, Sharp & Dohme, West Point, Pa.) was further purified by gel filtration on Ultragel® AcA-44 (LKB Instruments, Inc., Rockville, N.M.). *Erwinia carotovora* asparaginase (Microbiological Research Establishment, Salisbury, England) was provided by Pharmaceutical Resources Branch of the National Cancer Institute.

EXAMPLE 8

Determination of the Biochemical Characteristics of Asparaginase

The X-ray crystallographic structures of several microbial asparaginases have been elucidated (see Lubkowski, J. & Palm, N. (1996), supra). Recombinant *W. succinogenes* asparaginase which possesses acceptable clinical properties has the following characteristics: (1) catalytic activity in vitro, (2) preferably a native-protein-like homotetrameric structure required for functional enzymatic catalysis, and (3) with respect to the recombinant form of *W. succinogenes* asparaginase, similar to that of the native, homotetrameric form of *W. succinogenes* asparaginase, greater substrate specificity for L-asparagine and not catalyzing the deamidation of L-glutamine to any physiologically significant degree.

In order to quantitate the biochemical characteristics of both the native, homotetrameric and recombinant asparaginase enzymes, $K_m$ and $V_{max}$ enzyme kinetics, substrate specificity, pH optimum, and temperature optimum can be determined. In addition, SDS-PAGE under both reducing and non-reducing conditions, followed by silver and Coomassie Blue staining of the gels, can be utilized to establish enzyme homogeneity, evaluate subunit composition, and determine enzyme molecular weight (see Park, R. & Liu, K., A role for Shc, grb2 and raf-1 in FcR1 signal relay, 271. *J. Biol. Chem.* 13342 (1996).

The enzymatic activity of L-asparaginase can be quantitatively determined by the amount of ammonia produced upon the hydrolysis of 0.08 M L-asparagine using 0.01 M sodium phosphate buffer (pH 7.0) as the reaction buffer (see Durden, D. L. & Distasio, J. A. (1980), supra). The assay mixture can consist of 10 to 40 IU of a homogeneous solution of L-asparaginase enzyme diluted to 2.0 ml with 0.01 M sodium phosphate buffer (pH 7.0). Briefly, this assay system measures the deamidation of L-asparagine indirectly by quantitating the release of $NH_3$ as colormetrically-detected by Nessler's Reagent. A standard curve of $NH_4OH$ may be prepared to initially derive an extinction coefficient for $NH_3$, based upon absorbance at 420 nm. The enzyme reaction may be initiated by the addition of the L-asparagine substrate (0.04 M). For the determination of $K_m$ and $V_{max}$ enzyme kinetics, a more sensitive NADPH-dependent L-asparaginase assay system can utilized (see Distasio, J. A. & Niederman, T. (1976), supra).

EXAMPLE 9

Therapeutic Administration of Asparaginase in Murine Animal Models

The recombinant and native forms of *W. succinogenes* asparaginase may be titrated between 5 and 50 IU per injection and the mice can receive up to 3 daily intraperitoneal (I.P.) injections at each dose. Toxicological and pharmacological studies for the native and recombinant enzymes can be performed by the determination of serum enzyme activity (i.e., serum enzyme half-life) as described in Example 8.

EXAMPLE 10

Determination of Asparaginase Enzymatic Activity (Serum Half-Life)

Serum half-life determinations can be performed on Balb/c mice intraperitoneally-injected with 5 or 10 IU of native (WS) or recombinant (rWS) *Wolinelia succinogenes* asparaginase. Enzyme half-life measurements can be performed by a slight modification of a previously published procedure (see Durden, D. L., et al., kinetic analysis of hepatotoxicity associated with anti-neoplastic asparaginases, 43 *Cancer res.* 1602 (1983)). Specifically, enzyme half-life measurements can be performed by obtaining a 5 µl blood sample from the tail vein of the Balb/c mice at specific intervals following the I.P. injection of the WS or rWS asparaginase. The blood samples are then kept on ice until all samples had been collected. Once sampling was completed, each 5 µl blood sample can then be immediately pipetted into 0.5 ml of cold 1.19% sodium chloride in 0.1 M sodium phosphate buffer (pH 7.0) and mixed by vigorous vortexing.

To determine serum asparaginase activity (and hence serum half-life), two 0.2 ml aliquots from each time point can be equilibrated in a 37° C. water bath. The enzymatic reaction is subsequently initiated by the addition of 0.03 ml of 0.04 M L-asparagine, pre-equilibrated to 37° C. prior to addition, into one of the 0.2 ml samples. The other 0.2 ml aliquot receives only 0.3 ml of distilled water and will serve as a control "blank." The substrate-containing reaction tube may be incubated at 37 C. for 1 hour after which the reaction is stopped by the addition of 0.2 ml of 5% TCA. In addition, a 0.2 ml aliquot of 5% TCA is also added to the control "blank." The tubes are then centrifuged at 5000×g to remove the resulting TCA-produced precipitate. Enzymatic activity may be colormetrically-determined by the addition of a 0.2 ml aliquot of the substrate-containing sample to 0.2 ml of distilled water and 0.2 ml a freshly-prepared Nessler's Reagent and the absorbance at 420 nm is read using a spectrophotometer (Gilford Instrument Laboratories, Oberlin, Ohio).

EXAMPLE 11

Determination of the Anti-Neoplastic Activity of Asparaginase

The anti-neoplastic (anti-lymphoma) activity of homogeneous preparation of both native (WS) and recombinant (rWS) *W. succinogenes* asparaginase, as well as that of native *E. coli* (EC) and *E. carotovora* (Erw) asparaginases, can be determined utilizing the 6C3HED Gardner lymphosarcoma cell line implanted in C3H mice. This lymphoid tumor originated in the thymus of C3H mice given high doses of estradiol and was perpetuated by serial transplantation in the C3H mice. In these studies, the tumor is maintained as an ascites tumor through I.P injection of $2 \times 10^8$ viable lymphosarcoma cells in 0.1 ml of PBS (pH 7.0).

To determine asparaginase anti-tumor activity, $2.5 \times 10^6$ viable 6C3HED lymphosarcoma cells from an ascites tumor is injected in a volume of 0.05 ml of PBS (pH 7.0) subcutaneously in the left ventral groin of 9 to 12 week-old C3H mice. Similarly, in another series of experiments, $2.5 \times 10^4$ viable P1798 lymphosarcoma cells from an ascites tumor is injected in a volume of 0.05 ml of PBS (pH 7.0) subcutaneously in the left ventral groin of 9 to 12 week-old Balb/c mice (see Jack, G. W., et al., The effect of histidine ammonia-lyase on some murine tumors, 7 *Leukemia Res.* 421 (1983)). Palpable solid tumor growth generally occurred within 4 to 7 days after injection of the lymphosarcoma cells. Changes in solid tumor volume are then subsequently measured by daily caliper-based measurement of tumor dimensions along three axes. When the average tumor volume reaches 1 cm³, intraperitoneal injection of asparaginase can be performed. A total dosage of 3 or 6 IU of asparaginase may be administered in a total of six I.P injections of 0.5 or 1.0 IU asparaginase/injection, respectively. Injections may be administered twice daily for three consecutive days.

The negative control animal group receives I.P. injections of 0.01 M phosphate buffer (pH 7.0) utilizing a similar injection schedule. *E. coli* and *E. carotovora* asparaginases serve as positive controls for comparison of anti-tumor activity in this series of experiments. Student's t-test will be utilized for all statistical analysis of data.

EXAMPLE 12

Immune Cross-Reactivity *W. succinogenes* Asparaginase

This example describes how it was determined if antibodies in patients known to neutralize *E. coli* asparaginase react with *W. succinogenes*. Specifically, an ELISA assay was performed to make this determination, as described below.

The ELISA assay was performed on two 96 well microtiter plates, as follows: asparaginase (EC on one plate, WS on the other) was diluted in carbonate buffer (prepared by dissolving 1.59 g $Na_2CO_3$, $NaHCo_3$, and 0.2 g $NaN_3$ in 1 L of purified water; pH was adjusted to 9.0–9.5 using 1N HCl or 1N NaOH; the buffer was stored at 4° C. for no more than two weeks before use) to a final concentration of 0.10 IU/mL. 54 wells on each plate were coated with 100 µL of the respective diluted asparaginase solution and incubated overnight at 4° C. after being wrapped in aluminum foil to allow the enzyme to become associated with the plates.

The following morning the plates were removed and the solution from each of the wells was removed. These wells were then blocked with 300 µL of a 1 mg/mL solution of BSA-PBS blocking buffer, pH 7.0 (prepared fresh by adding the appropriate amount of bovine serum albumin to PBS buffer, 0.010 M sodium phosphate, pH 7.0–7.2, 0.9% saline). The plates were then incubated for 1 hour at room temperature. Thereafter, the plates were washed with 300 mL of saline-Tween buffer (0.145 M NaCl, 0.05% Tween 20) per well using a Dynatech Ultrawash plate washer.

The antibodies used to screen the two plates were diluted as follows: 1:100, 1:1,000; 1:2,000; 1:4,000; 1:8,000; 1:16,000; and 1:32,000. As a control, serum from a normal human patient was used. Patient serum and rabbit anti-EC asparaginase serum and normal human serum were diluted in PBS-Tween (PBS containing 0.05% Tween 20) and 100 µL of each dilution was placed on each plate in triplicate according to the following grid:

| CONTROL | | | HUMAN PATIENT | | | RABBIT ANTIBODIES | | |
|---|---|---|---|---|---|---|---|---|
| 1 | 2 | 3 | 1 | 2 | 3 | 1 | 2 | 3 |
| 1:1,000 | 1:1,000 | 1:1,000 | 1:1,000 | 1:1,000 | 1:1,000 | 1:1,000 | 1:1,000 | 1:1,000 |
| 1:2,000 | 1:2,000 | 1:2,000 | 1:2,000 | 1:2,000 | 1:2,000 | 1:2,000 | 1:2,000 | 1:2,000 |
| 1:3,000 | 1:3,000 | 1:3,000 | 1:3,000 | 1:3,000 | 1:3,000 | 1:3,000 | 1:3,000 | 1:3,000 |
| 1:4,000 | 1:4,000 | 1:4,000 | 1:4,000 | 1:4,000 | 1:4,000 | 1:4,000 | 1:4,000 | 1:4,000 |
| 1:8,000 | 1:8,000 | 1:8,000 | 1:8,000 | 1:8,000 | 1:8,000 | 1:8,000 | 1:8,000 | 1:8,000 |
| 1:16,000 | 1:16,000 | 1:16,000 | 1:16,000 | 1:16,000 | 1:16,000 | 1:16,000 | 1:16,000 | 1:16,000 |
| 1:32,000 | 1:32,000 | 1:32,000 | 1:32,000 | 1:32,000 | 1:32,000 | 1:32,000 | 1:32,000 | 1:32,000 |

After adding the above dilutions, the plates were incubated for at least 1.5 hour at room temperature, followed by washing each plate three times with saline-Tween as described above. A 1:1,000 dilution of Horse radish peroxidase-conjugated goat anti-human immunoglobulin (BioSource International) was then prepared in PBS-Tween. 100 µL of the HP-conjugated anti-human Ig was then added to each well. The plates were then covered and allowed to incubate at room temperature for 1 hour.

After the 1 hour incubating each plate was again washed three times with saline-Tween, as before. To detect antibody binding, 100 µL of OPD (o-phenylenediaminedihydrochloride) substrate (40 mg of OPD in 100 mL a citrate phosphate buffer (0.1M, pH 6.0, prepared by combining a solution containing 13.4 g $Na_2HPO_4 7H_2O$ (dibasic) in 500 mL distilled water with an amount of a solution containing 9.60 g citric acid (anhydrous) in 500 mL distilled water sufficient to adjust the pH to 6.0) with 334 µL of 3% $H_2O_2$ prepared immediately before use and kept at room temperature in the dark) was added to each well and allowed to incubate at room temperature in the dark for approximately 40 minutes. The reaction in each well was stopped by adding 100 µL of 1 M phosphoric acid. The absorbance of each well was then measured at 40 nm.

As is shown in FIG. 8, high titer neutralizing antibodies against the *E. coli* enzyme present in patient plasma failed to bind to the *Wolinella* asparaginase. This figure shows one of 6 plasma specimens collected from patients known to be allergic to the *E. coli* enzyme as well as rabbit antisera raised against the *E. coli* asparaginase. None of these anti-*E. coli* reactive antisera bind or neutralize the *Wolinella* asparaginase activity (FIGS. 8 and 9). From these data it was concluded that the *W. succinogenes* enzyme is immunologically distinct from *E. coli*, and that the *Wolinella* enzyme can be used in patients allergic to the *E. coli* enzyme (as exemplified by titration of patient plasma shown in FIG. 8 and rabbit anti-*E. coli* antisera shown in FIG. 9).

A highly specific antisera against the *W. succinogenes* enzyme which does not cross react with *E. coli* asparaginase in Western blot analysis has also been prepared. This reagent is useful for performing immunological characterizations of the native, recombinant, and various analog forms of the *Wolinella* enzyme. Analysis of native, recombinant, and analog forms of *W. succinogenes* asparaginase for this type of immunologic cross reactivity will be useful in characterization of genetically and chemically modified proteins. Importantly, these analyses will be applied to analysis of clinical specimens during phase I and II clinical trials of the different forms of the *W. succinogenes* enzyme.

EXAMPLE 13

Methodology for Protein Modification using Acylation

Protein acylation is accomplished by using different acylating agents, such as acyl halides (e.g., acyl chlorides), carbodiimide compounds, or acid anhydrides, each with a different number of carbon atoms comprising a straight or branched aliphatic chain attached to the carbonyl, or the modified carbonyl (in the case of carbodiimides), carbon atom. The acylating agents contemplated for use in practicing this invention have the ability to react with a polar group contained within the peptide sequence of a protein to form an amide side chain. The polar group is the side chain of any of the amino acids in the primary sequence, for example, the amine group of lysine or arginine, the hydroxy group of threonine, serine, or tyrosine, or the thiol group of cysteine. Preferably, the reaction is carried out under conditions which do not substantially reduce (i.e., reduce by more than 90%, preferably less than 50%, and more preferably less than 25%) the catalytic activity of the enzyme.

Briefly, the chemical reaction was started at zero time with the dropwise addition of acetyl chloride to 5,000 IU of asparaginase, derived from either *E. coli* or *W. succinogenes*, in a volume of 10 mL of 0.1 M borate buffer at pH 8.5. The final concentration of each acid chloride is 0.1 M. The chemical reaction involves a nucleophilic attach of the polar group, e.g. the free amino group, within the peptide sequence of the protein, e.g. asparaginase molecule, (which is maintained in an unprotonated form in the borate buffer, pH 8.5) with the reactive acylating agent. The polar group reacts with the acylating agent yielding an aliphatic hydrocarbon modified amino acid side chain. If the acylating agent is an acyl halide, an equivalent of the respective hydrohalic acid is produced. Thus, if the acylating agent is acyl chloride and the amino acid to be modified is lysine, then the reaction yields an acylated amino group and 1 equivalent of HCl (see FIG. 7). To prevent acid conditions from destroying the structure of the protein molecule (decreasing yield of enzyme, Table 1, below), a 1 N solution of NaOH is added drop-wise to the reaction mixture every 5–10 seconds. Aliquots of 2 mL were removed at the indicated reaction times (see Table 1, below), and immediately dialyzed against 0.01 M phosphate buffer at pH 7.0. Protein concentration is measured by Bradford method. Enzyme activity is determined by the amount of ammonia produced upon hydrolysis of L-asparagine (0.08 M L-asparagine) with a Nessler's reagent (see Durden, D. L. et al., *Cancer Res.* 40: 1125, (1980)). Free amino groups are measured by the method of Habeeb (see Habeeb, A. F. S. A., *Analytical Biochemistry*, 14:328, 1966).

TABLE I

Effect of acylation with
acetyl chloride on *W. succinogenes* asparaginase

| | Reaction time[a] (hr) | Specific activity[b,c] (IU/mg) | Reduction of free amines[d] (%) | Recovery of activity[a] (%) | Half-Life (hr) |
|---|---|---|---|---|---|
| Native enzyme | 0 | 150.0 | 0 | 100.0 | 1.8 |
| Derivatized enzyme | 0.5 | 120.0 | 29.0 | 80.0 | 8.0 |
| | 1.0 | 129.0 | 26.8 | 86.0 | 8.2 |
| | 2.0 | 130.0 | 32.4 | 86.6 | 7.4 |
| | 3.0 | 120.0 | 30.2 | 80.0 | 7.3 |
| | 4.5 | 90.0 | 31.3 | 60.0 | 6.2 |

[a]The reaction is started at time 0 with the addition of acetyl chloride to 5,000 IU of *W. succinogenes* asparaginase in 10 ml of 0.1M borate buffer, pH 8.5. Aliquots of 2.0 ml are removed at the times indicated and dialyzed against 0.01M phosphate buffer, pH 7.0.
[b]Protein is measured in triplicate by method of Bradford.
[c]Enzyme activity is measured by determining the amount of ammonia produced upon hydrolysis of L-asparagine with Nessler's reagent.
[d]Free amino groups are measured by method of Habeeb.

Acyl modification is performed with acylating agents of different aliphatic chain lengths, e.g., a 2 carbon aliphatic chain (C2), a 4 carbon aliphatic chain (C4), a 6 carbon aliphatic chain (C6), etc. Importantly, each specific protein (e.g., asparaginase) has different numbers of free polar groups in different positions within the protein molecule and hence each protein is optimally modified with a different length acylating agent which conjugates a different aliphatic carbon chain to the free amino groups. These include, for example, acetyl chloride (C2), butyryl chloride (C4), hexanoyl chloride (C6), decanoyl chloride (C10), as well as the use of branched chain chlorides including trimethylacetyl chloride. Also, different acylating agents may be used for different proteins. For example, with some proteins acetyl chloride may be used, whereas for other proteins acetic anhydride may be the best acylating agenst. By way of illustration, the covalent modification of the *W. succinogenes* asparaginase with the acetyl chloride is presented in Table 1.

A. Results of Modification

There are a number of problems that have been associated with the use of enzymes for therapeutic purposes. Many of these enzymes have extremely short half-lives which severely limits their effectiveness in vivo. The modification of proteins using organic modification techniques of the present invention is a promising solution to many of these problems. The C2 modification of *W. succinogenes* asparaginase results in an enzyme which has a half-life of 8.2 hours in mice as compared to the 1.8 hour half-life of the native enzymes. The increase in half-life is consistent with the time course of acetylation reaction (resulting in 20–40% decrease in enzyme activity while the activity of the *W. succinogenes* asparaginase decreases with the increasing reaction time). An about 80% recovery of enzyme activity after a 30 min. reaction time was observed, a time of maximum alteration of pharmacokinetic extension of half-life to 8.0 hours. Other modification procedures which involve polymerization (e.g., polyethylene-glycol modification) result in heterogenous groups of modified reaction products which may not be suitable for administration in humans. The acid chloride modification procedure is a systematic approach which does not yield such heterogeneity in reaction products (see FIG. 7). The greater reproducibility and more restricted nature of reaction products result in a well controlled modification of proteins and a more reliable product with predictable extension of half-life which decrease the immunogenicity, and with the advantage of being able to very carefully control the extent of modification of the polar groups present in a specific protein molecule. Current data modifying *W. succinogenes* asparaginase demonstrate that the enzyme is modified with a C2 acylation reaction which results in the augmentation of half-life approximately four fold. The modification of the free amino groups and the asparaginase molecule is responsible for extension of half-life. It is suggested that the extension of half-life will correlate with a decrease in the electrostatic charge, increase in hydrophobicity and decreased immunogenicity of the *Wolinella* enzyme. The extension of half-life and decreased immunogenicity will increase the efficacy of the *W. succinogenes* enzyme when this drug is used in the treatment of acute lymphoblastic leukemia, autoimmune disease, or AIDS, for example, in humans. Through this modification procedure, we are able to generate foreign proteins which have lower immunogenicity, extended half-life, and augmented efficacy. With this systematic approach of modification, any protein can be modified and the modified protein can then be used in the treatment of human disease. Essentially, any protein that has polar groups available in its native state (essentially all known proteins) is amenable to the modification technique of the present invention. Hence this invention extends to all proteins currently used in treatment of human, animal and plant diseases.

While embodiments and applications of the present invention have been described in some detail by way of illustration and example for purposes of clarity and understanding, it would be apparent to those individuals whom are skilled within the relevant art that many additional modifications would be possible without departing from the inventive concepts contained herein. The invention, therefore, is not to be restricted in any manner except in the spirit of the appended claims.

All references cited herein are hereby incorporated in their entirety. When used above, the term "including" means "including, without limitation," and terms used in the singular shall include the plural, and vice versa, unless the context dictates otherwise.

I claim:

1. A method of producing a recombinant *Wolinella succinogenes* asparaginase analog containing a N-terminal tag, the method comprising the steps of:
   (a) obtaining a nucleic acid molecule comprising the nucleotide sequence of SEQ ID NO: 3;
   (b) cloning the nucleic acid sequence into an expression vector;
   (c) introducing the expression vector into a suitable host cell or cells;
   (d) culturing the host cell(s) under conditions that allow expression of the asparaginase from the expression vector in biologically active form or in a form from which biological activity can be reconstituted; and (e) subjecting the asparaginase to modification by acylation with one or more acyl halides, wherein the modified asparaginase has asparaginase enzyme activity.

2. The method of claim 1, further comprising the step of isolating said asparaginase.

3. The method of claim 1, wherein said method is performed in vivo.

4. The method of claim 1, wherein said expression vector is carried in a gene delivery vehicle.

5. The method of claim 4 wherein said gene delivery vehicle is selected from the group consisting of a recombinant virus and a non-viral gene delivery system.

6. The method of claim 2, wherein said polypeptide is an analog *Wolinella succinogenes* asparaginase.

7. The method of claim 2, wherein said polypeptide is covalently modified by a process selected from the group consisting of acylation and pegylation.

8. The method of claim 7, wherein said acylation is accomplished by using one or more acyl halides.

9. A composition comprising a purified recombinant *Wolinella succinogenes* asparaginase analog, obtained by the method of claim 1.

10. The composition of claim 9, further comprising a pharmaceutically acceptable carrier.

* * * * *